(12) United States Patent
Yamamoto et al.

(10) Patent No.: US 11,512,108 B2
(45) Date of Patent: Nov. 29, 2022

(54) METHOD FOR PRODUCING AMIDE COMPOUND

(71) Applicant: CHUBU UNIVERSITY EDUCATIONAL FOUNDATION, Aichi (JP)

(72) Inventors: Hisashi Yamamoto, Aichi (JP); Wataru Muramatsu, Aichi (JP); Tomohiro Hattori, Aichi (JP)

(73) Assignee: CHUBU UNIVERSITY EDUCATIONAL FOUNDATION, Aichi (JP)

( * ) Notice: Subject to any disclaimer, the term of this patent is extended or adjusted under 35 U.S.C. 154(b) by 42 days.

(21) Appl. No.: 17/047,464

(22) PCT Filed: Apr. 25, 2019

(86) PCT No.: PCT/JP2019/017786
§ 371 (c)(1),
(2) Date: Oct. 14, 2020

(87) PCT Pub. No.: WO2019/208731
PCT Pub. Date: Oct. 31, 2019

(65) Prior Publication Data
US 2021/0147473 A1    May 20, 2021

(30) Foreign Application Priority Data
Oct. 30, 2018   (JP) .............................. JP2018-204489

(51) Int. Cl.
| C07K 1/08 | (2006.01) |
| C07K 1/00 | (2006.01) |
| C07C 231/02 | (2006.01) |
| C07K 1/02 | (2006.01) |

(52) U.S. Cl.
CPC ............ C07K 1/003 (2013.01); C07C 231/02 (2013.01); C07K 1/02 (2013.01); C07K 1/08 (2013.01)

(58) Field of Classification Search
CPC .. C07K 1/003; C07K 1/02; C07K 1/08; C07C 231/02; C07C 269/06; C07C 319/20; C07F 7/10
See application file for complete search history.

(56) References Cited

U.S. PATENT DOCUMENTS

| 11,370,747 B2 * | 6/2022 | Yamamoto ............ C07C 231/02 |
| 2020/0131117 A1 | 4/2020 | Yamamoto et al. |

FOREIGN PATENT DOCUMENTS

| CN | 102250124 A | 11/2011 |
| EP | 3 466 922 A1 | 4/2019 |
| EP | 3 617 185 A1 | 3/2020 |

| WO | 2009/060843 A1 | 5/2009 |
| WO | 2017/204144 A1 | 11/2017 |
| WO | 2018/199146 A1 | 11/2018 |
| WO | 2018/199147 A1 | 11/2018 |

OTHER PUBLICATIONS

Allen et al, Chem.Commun., 2012, 48, 666-668 (Year: 2012).*
Tozawa et al., Chemistry Letters, 2005, 34, 5, 734-735 (Year: 2005).*
International Search Report dated Dec. 28, 2020 corresponding to PCT/JP2020/040960 filed Oct. 30, 2020; 3 pages. English translation.
International Search Report dated Feb. 2, 2021 corresponding to PCT/JP2020/040951 filed Oct. 30, 2020; 5 pages. English translation.
Akpoyraz, M., Silicon tetrachloride and alkylchlorosilanes in the synthesis of amides from carboxylic acids and amines, *Doga Bilim Dergisi Seri C: Tip* (1980) 4(2):1-4. See, English Abstract.
Jikken Kagaku Koza Edition 5, Book 16, Yuuki Kagobutsu No Gosei IV (2005), pp. 259-260 and 268-269 in particular, experiment examples 2.75, 2.86 Maruzen publish Co., Ltd.); See, Partial Translation in English.
Muramatsu, Wataru et al., "Substrate-Directed Lewis-Acid Catalysis for Peptide Synthesis," *Journal of the American Chemical Society* (Jul. 16, 2019) 141(31):12288-12295.
Schmidt, Michael A. et al., "Development of a Two-Step, Enantioselective Synthesis of an Amino Alcohol Drug Candidate," *Organic Process Research & Development* (Jul. 2, 2015) 19(9):1317-1322.

(Continued)

*Primary Examiner* — Sudhakar Katakam
(74) *Attorney, Agent, or Firm* — Mintz, Levin, Cohn, Ferris, Glovsky and Popeo, P.C.

(57) ABSTRACT

Provided is a novel method whereby an amide compound can be produced by highly stereoselectively and efficiently performing amidation between a plurality of amino acids and/or peptides. A compound of general formula (3) is synthesized by forming an amide bond between the carboxyl group on the right side of general formula (1) in a compound represented thereby and the amino group on the left side of general formula (2) in a compound represented thereby, in the presence of a Lewis acid catalyst and a silylating agent [in formulae (1), (2) and (3), each symbol has the same meaning as defined in claims].

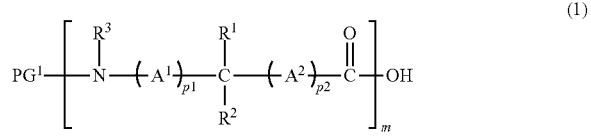

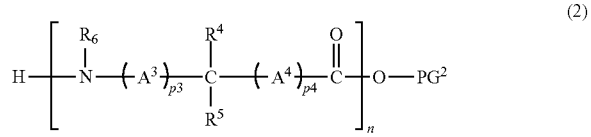

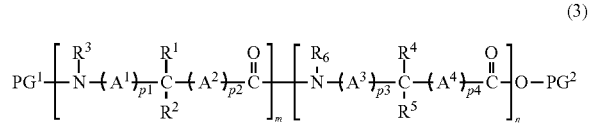

6 Claims, 4 Drawing Sheets

(56) References Cited

OTHER PUBLICATIONS

Tozawa, Takashi et al., "An efficient method for the preparation of carboxamides by dehydration condensation using tretrakis (1,1,1,3,3,3-hexafluoro-2-propxy) silane," *Chemistry Letters* (2005; published on the web Oct. 27, 2005) 34(12):1586-1587.

Tozawa, Takashi et al., "A convenient method for preparations of 1-acylimidazoles and carboxamides by using novel imidazolylsilane derivatives," *Chemistry Letters* (2005; published on the web Apr. 22, 2005) 34(5):734-735.

International Search Report dated Jul. 24, 2018 corresponding to PCT/JP2018/016767 filed Apr. 25, 2018; 2 pages. English translation.

Allen, C. Liana et al., "Direct amide formation from unactivated carboxylic acids and amines," *Chem. Commun.* (2012; accepted Nov. 8, 2011) 48:666-668.

Davie, Elizabeth A. Colby et al., "Asymmetric Catalysis Mediated by Synthetic Peptides," *Chem Rev.* (2007; published on Web Dec. 12, 2007) 107:5759-5812.

Han, Chong et al., "Catalytic Ester-Amide Exchange Using Group (IV) Metal Alkoxide-Activator Complexes," *j. am. Chem. Soc.* (Published on Web Jun. 23, 2005) 127:10039-10044.

Isidro-Llobet, Albert et al., "Amino Acid-protecting Groups," *Chem. Rev.* (2009; rec'd Apr. 28, 2008) 109:2455-2504.

Kinoshita, Hideki et al., "The Cinnamyloxycarbonyl Group as a New Amino-Protecting Group," *Chemistry Letters* (© 1985 The Chemical Society of Japan) pp. 515-518.

Minami, Ichiro et al., "1-Isopropylallyloxycarbonyl (IPAoc) as a Protective Group of Amines and Its Deprotection Catalysed by Palladium-Phosphine Complex," *Tetrahedron Letters* (1987 Rec'd in Japan Jan. 31, 1987) 28(24):2737-2740.

Ohshima, Takashi et al., "sodium methoxide: a simple but highly efficient catalyst for the direct amidaiton of esters," *Chem. Commun.* (Accepted Apr. 12, 2012) 48:5434-5436.

Roos, Eric C. et al., "Palladium-Catalyzed Transprotection of Allyloxycarbonyl-Protected Amines: Efficient One-Pot Formation of Amides and Dipepetides," *J. Org. Chem.* (1995 Abstract published in *Advance AC Abstracts* Mar. 1, 1995) 60:1773-1740.

Supplementary European Search Report dated Dec. 10, 2020 corresponding to EP18789973.7 filed Apr. 25, 2018; 5 pages.

Fang, Jiang Bao et al., "Tantalum pentachloride as a coupling agent for stereohindered amide bond formation," *Inoorganica Chimica ACTA* (Jul. 1, 2004) 357(9):2415-2426.

International Search Report dated Jul. 30, 2019 corresponding to PCT/JP2019/0177867 filed Apr. 25, 2019; 1 page. English translation.

Bode, Jeffrey W. et al., "Chemoselective Amide Ligations by Decarboxylative Condensations of N-Alkylhydroxylamines and α-Ketoacids," *Angew. Chem. Int. Ed.* (Published online Jan. 17, 2006) 45:1248-1252.

Colby Davie, Elizabeth A. et al., "Asymmetric Catalysis Mediated by Synthetic Peptides," *Chem. Rev.* (Published on Web Dec. 12, 2007) 107:5759-5812.

De Figueiredo, Renata Marcia et al., "Nonclassical Routes for Amide Bond Formation," *Chemical Reviews* (Sep. 22, 2016) 116:12029-12122.

Dunetz, Joshua R. et al., "Large-Scale Applications of Amide Coupling Reagents for the Synthesis of Pharmaceuticals," *Organic Process Research & Development* (2016; published Nov. 15, 2015) 20:140-177.

El-Faham, Ayman et al., "Peptide Coupling Reagents, More than a Letter Soup," *Chemical Reviews* (Aug. 26, 2011) 111:6557-6602.

Montalbetti, Christian A. G. N. et al., "Amide bond formation and peptide coupling," *Tetrahedron* (available online Sep. 19, 2005) 61:10827-10852.

Nilsson, Bradley L. et al., "Chemical Synthesis of Proteins," *Annu. Revi. Biophys. Biomol. Struct* (first published online as a Review in Advbance on Jan. 24, 2005) 34:91-118.

Schnölzer, Martina et al., "Constructing Proteins by Dovetailing Unprotected Synthetic Peptides: Backbone-Engineered HIV Protease," *Science* (Apr. 10, 1992) 256:221-225.

Tsuji, Hiroaki et al., "Hydroxy-Directed Amidation of Carboxy lie Acid Esters Using a Tantalum Alkoxide Catalyst," *Journal of the American Chemical Society* (Oct. 16, 2016) 183:14218-14221.

* cited by examiner

METHOD FOR PRODUCING AMIDE COMPOUND

FIELD

The present invention pertains to a method for producing an amide compound.

BACKGROUND ART

Conventionally, amide compounds represented by peptides have been used in a wide variety of fields, including pharmaceuticals, cosmetics, and functional foods. Development of synthetic methods thereof has been diligently pursued as an important research goal in synthetic chemistry (NPTL 1 to 6). However, there are not many catalysts that are effective for the amidation reaction, which is the most important reaction in peptide synthesis. Therefore, it is necessary to use an equivalent reagent that forms by-products, and thus, peptide synthesis, which involves repeating multi-stage reactions, is extremely inefficient from the viewpoint of atom economy (atomic yield). The amount of by-products is large, and there are few effective purification means. As a result, the cost of disposal of by-products and purification constitutes most of the necessary costs for peptide synthesis, and is the largest obstacle to development in this field.

In peptide synthesis, which uses amino acids or derivatives thereof as starting materials, it is desirable for the amidation reaction to proceed with high stereoselectivity. Enzyme reactions in the body are examples of highly stereoselective amidation reactions. For example, in the body, peptides are synthesized with extremely high stereoselectivity through sophisticated use of enzymes and hydrogen bonds. However, enzyme reactions are not suitable for mass production, requiring enormous financial and time costs when applied to synthetic chemistry.

In synthetic chemistry, amidation reactions using catalysts have been examined, but in conventional means, the amide bond is formed primarily through the method of activating carboxylic acid, such that racemization occurs quickly, whereby synthesizing a peptide with high stereoselectivity and efficiency is difficult.

The present inventors have found that an amide compound can be synthesized with high chemoselectivity via amidation of a hydroxy ester compound in the presence of a specific metal catalyst and have already filed a patent application (PTL 1). Although this method is excellent, methods applicable to a wide range of amino acids and derivatives thereof are demanded.

According to conventional methods, it is very difficult to link an additional amino acid or derivative to a peptide comprising a plurality of amino acids or derivatives thereof (chemical ligation) or link two or more peptides via amide bonds. As an amidation method for ligation to such peptides, there are known a method for ligation by using an amino acid having a sulfur atom to utilize the high reactivity of the sulfur atom (NPL 7) and a method for ligation by synthesizing an amino acid hydroxyamine to utilize the high reactivity of the hydroxyamine (NPL 8). However, in the former method, it is difficult to synthesize amino acids having a sulfur atom, and in the latter method, hydroxyamine synthesis involving several steps is necessary. Both methods are time-consuming and costly and have a disadvantage in efficiency.

CITATION LIST

Patent Literature

[PTL 1] WO 2017/204144

Non-Patent Literature

[NPL 1] Annu. Rev. Biophys. Biomol. Struct., 2005, 34, 91-118
[NPL 2] Tetrahedron, 2005, 6, 10827-10852
[NPL 3] Chem. Rev., 2007, 107, 5759-5812
[NPL 4] Chem. Rev., 2011, 111, 6557-6602
[NPL 5] Org. Process Res. Dev., 2016, 20(2), 140-177
[NPL 6] Chem. Rev., 2016, 116, 12029-12122
[NPL 7] Science, 1992, 256, 221-225
[NPL 8] Angew. Chem. Int. Ed., 2006, 45, 1248-1252

SUMMARY

Technical Problem

Under these circumstances, a method capable of highly stereoselectively and efficiently causing amidation to produce an amide compound and a method capable of causing amidation of a peptide to produce an amide compound are demanded.

One primary object of the present invention is to provide a novel method capable of highly stereoselectively and efficiently causing amidation between a plurality of amino acids to produce an amide compound.

Another primary object of the present invention is to provide a novel method capable of linking via an amide bond an additional amino acid or peptide to a peptide comprising a plurality of amino acids or derivatives thereof to produce an amide compound.

Solution to Problem

As a result of intensive investigations, the present inventors have found that a terminal carboxyl group of a first amino acid or peptide having a protected amino group and a terminal amino group of a second amino acid or peptide having a protected carboxyl group are linked together by forming an amide bond therebetween in the presence of a Lewis acid catalyst and a silylating agent, whereby an amide compound can be produced with high stereoselectivity and efficiency. Further, the present inventors have found that this method is applicable to the production of amide compounds via a linkage between a peptide and an amino acid or a linkage between peptides. Accordingly, the present invention has been achieved.

Specifically, one aspect of the present invention relates to a method for producing an amide compound, comprising a step of forming an amide bond between a carboxyl group on the right side of the undermentioned general formula (1) of a compound represented by general formula (1) and an amino group on the left side of the undermentioned general formula (2) of a compound represented by general formula (2) in the presence of a Lewis acid catalyst and a silylating agent to synthesize a compound represented by the undermentioned general formula (3).

Advantageous Effect

According to the present invention, it is possible to highly stereoselectively and efficiently cause amidation and to thereby produce an amide compound.

Further, according to the present invention, it is possible to link via an amide bond an additional amino acid or peptide to a peptide comprising a plurality of amino acids or derivatives thereof and to thereby produce an amide compound.

DESCRIPTION OF EMBODIMENTS

Figure 1A:
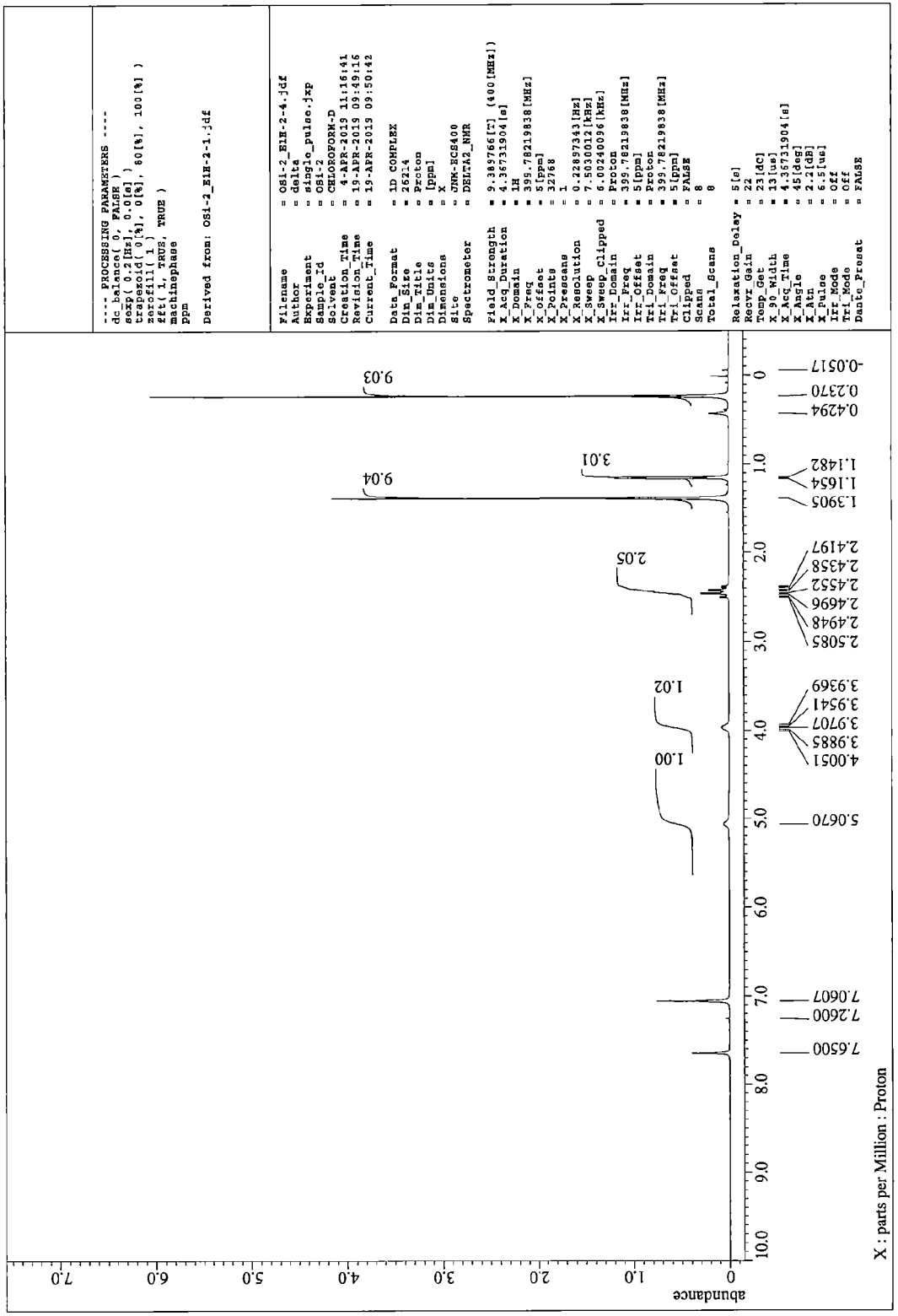
FIG. 1A depicts a $^1$H-NMR spectrum obtained in Reference Example 1.

The present invention is described hereinafter in detail with reference to specific embodiments thereof. However, the present invention is not limited to the following embodiments and can be carried out in any embodiment that does not deviate from the gist of the present invention.

All the patent publication, unexamined patent publications, and non-patent literature cited in the present disclosure are incorporated herein by reference in their entireties for any purpose.

Definition of Terms

In the present disclosure, "amino acid" refers to a compound having a carboxyl group and an amino group. Unless otherwise specified, the type of amino acid is not particularly limited. For example, from the viewpoint of optical isomerism, the amino acid may be a D-amino acid or L-amino acid. From the viewpoint of the relative positions of the carboxyl group and the amino group, the amino acid may be any of an α-amino acid, β-amino acid, γ-amino acid, and δ-amino acid.

In the present disclosure, "peptide" refers to a compound comprising a plurality of amino acids linked together via peptide bonds. Unless otherwise specified, the plurality of amino acid units constituting the peptide may be the same type of amino acid unit or may consist of 2 or more types of amino acid units.

In the present disclosure, "amino group" refers to a functional group represented by any formula of —NH$_2$, —NRH, and —NRR' (where R and R' each represent a substituent) obtained by removing hydrogen from ammonia, a primary amine, and a secondary amine, respectively.

In the present disclosure, unless otherwise specified, the hydrocarbon group may be aliphatic or aromatic. The aliphatic hydrocarbon group may be a chain or a ring. The chain hydrocarbon group may be linear or branched. The cyclic hydrocarbon group may be monocyclic, bridged cyclic, or Spiro cyclic. The hydrocarbon group may be saturated or unsaturated. In other words, one, two, or more carbon-carbon double and/or triple bonds may be included. Specifically, "hydrocarbon group" represents a concept including an alkyl group, alkenyl group, alkynyl group, cycloalkyl group, cycloalkenyl group, cycloalkynyl group, aryl group, etc. Unless otherwise specified, one, two, or more hydrogen atoms of the hydrocarbon group may be replaced with any substituents and one, two, or more carbon atoms of the hydrocarbon group may be replaced with any heteroatoms corresponding to the valence thereof.

In the present disclosure, "hydrocarbonoxy group" refers to a group comprising an oxy group (—O—) linked via one bond thereof to the hydrocarbon group as defined above.

In the present disclosure, "hydrocarbon-carbonyl group" refers to a group comprising a carbonyl group (—C(=O)—) linked via one bond thereof to the hydrocarbon group as defined above.

In the present disclosure, "hydrocarbon-sulfonyl group" refers to a group comprising a sulfonyl group (—S(=O)$_2$—) linked via one bond thereof to the hydrocarbon group as defined above.

In the present disclosure, the heterocyclic group may be saturated or unsaturated. In other words, one, two, or more carbon-carbon double and/or triple bonds may be included. The heterocyclic group may be monocyclic, bridged cyclic, or spiro cyclic. The heteroatom included in the constituent atoms of the heterocyclic group is not particularly limited, but examples thereof include nitrogen, oxygen, sulfur, phosphorus, and silicon.

In the present disclosure, "heterocyclicoxy group" refers to a group comprising an oxy group (—O—) linked via one bond thereof to the heterocyclic group as defined above.

In the present disclosure, "heterocycliccarbonyl group" refers to a group comprising a carbonyl group (—C(=O)—) linked via one bond thereof to the heterocyclic group as defined above.

In the present disclosure, "heterocyclicsulfonyl group" refers to a group comprising a sulfonyl group (—S(=O)$_2$—) linked via one bond thereof to the heterocyclic group as defined above.

In the present disclosure, unless otherwise specified, "substituents" are not particularly limited as long as the amidation step of the production method of the present invention proceeds, and each independently refer to any substituent. Examples include, but are not limited to, a halogen atom, hydroxy group, carboxyl group, nitro group, cyano group, thiol group, sulfonic acid group, amino group, amide group, imino group, imide group, hydrocarbon group, heterocyclic group, hydrocarbonoxy group, hydrocarbon-carbonyl group (acyl group), hydrocarbonoxycarbonyl group, hydrocarbon-carbonyloxy group, hydrocarbon-substituted amino group, hydrocarbon-substituted aminocarbonyl group, hydrocarbon-carbonyl-substituted amino group, hydrocarbon-substituted thiol group, hydrocarbon-sulfonyl group, hydrocarbonoxysulfonyl group, hydrocarbon-sulfonyloxy group, heterocyclicoxy group, heterocycliccarbonyl group, heterocyclicoxycarbonyl group, heterocycliccarbonyloxy group, heterocyclicamino group, heterocyclicaminocarbonyl group, heterocycliccarbonyl-substituted amino group, heterocyclic-substituted thiol group, heterocyclicsulfonyl group, heterocyclicoxysulfonyl group, and heterocyclicsulfonyloxy group. Further, "substituents" include functional groups comprising any of the functional groups above further substituted with any of the functional groups above as long as the valence and physical properties thereof permit. When any of the functional groups above has substituents, the number thereof is not particularly limited as long as the valence and physical properties thereof permit. When there are a plurality of substituents, they may be the same or different.

In the present disclosure, Me represents a methyl group, Et represents an ethyl group, Pr represents a propyl group, i-Pr represents an isopropyl group, Bu represents a butyl group, and t-Bu represents a tert-butyl group.

In the present disclosure, Ac represents an acetyl group, acac represents an acetylacetonate, Cp represents a cyclopentadienyl, Tf represents a trifluoromethanesulfonyl, Trt represents a trityl group, and THF represents a tetrahydrofuran.

In the present disclosure, amino acids and residues thereof are sometimes represented by three-letter abbreviations well known to a person skilled in the art. The three-letter abbreviations of major amino acids are shown in the following table.

TABLE 1

| Ala | alanine |
|---|---|
| Arg | arginine |
| Asn | asparagine |
| Asp | aspartic acid |
| Cys | cysteine |
| Gln | glutamine |
| Glu | glutamic acid |
| Gly | glycine |
| His | histidine |
| Ile | isoleucine |
| Leu | leucine |
| Lys | lysine |
| Met | methionine |
| Phe | phenylalanine |
| Phg | phenylglycine |
| Pro | proline |
| Ser | serine |
| Thr | threonine |
| Trp | tryptophan |
| Tyr | tyrosine |
| Val | valine |

In the present disclosure, β-homoamino acids and residues thereof are sometimes represented by "Ho" followed by three-letter abbreviations of corresponding α-amino acids.

Summary of the Production Method of the Present Invention

The present invention relates to a method for producing an amide compound (hereafter referred to as "the production method of the present invention" as appropriate), comprising a step of forming an amide bond (hereafter referred to as "amidation step" as appropriate) between a caroboxyl group on the right side of general formula (1) of a compound represented by general formula (1) (hereafter referred to as "compound (1)" as appropriate) and an amino group on the left side of general formula (2) of a compound represented by general formula (2) (hereafter referred to as "compound (2)" as appropriate) in the presence of a Lewis acid catalyst and a silylating agent to synthesize a compound represented by general formula (3) (hereafter referred to as "compound (3)" as appropriate).

[Chem. 1]

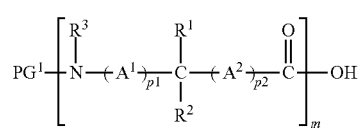

(1)

[Chem. 2]

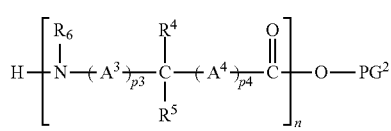

(2)

[Chem. 3]

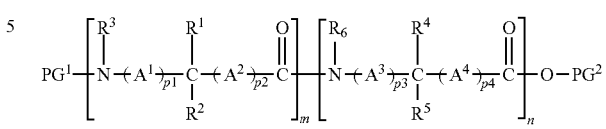

(3)

In other words, compound (1) corresponds to an amino acid or peptide having an amino group protected by $PG^1$ on the left side of its formula and a carboxylic acid on the right side of its formula. Further, compound (2) corresponds to an amino acid or peptide having an amino group on the left side of its formula and a carboxylic acid protected by $PG^2$ on the right side of its formula. Compound (3) corresponds to a peptide comprising the carboxylic acid on the right side of the formula of compound (1) and the amino group on the left side of the formula of compound (2) linked together via a formed amide bond.

According to the production method of the present invention, compound (1) and compound (2) are contacted together in the presence of a Lewis acid catalyst and a silylating agent to form an amide bond between the carboxyl group on the right side of the formula of compound (1) and the amino group on the left side of the formula of compound (2), whereby compound (3) is produced.

As a characteristic of the production method of the present invention, it is possible to highly stereoselectively and effectively cause amidation between a plurality of amino acids and to thereby produce an amide compound. As another characteristic, it is possible to link via an amide bond an additional amino acid or peptide to a peptide comprising a plurality of amino acids or derivatives thereof and to thereby produce an amide compound composed of more amino acids. Specifically, according to the production method of the present invention, it is possible to highly stereoselectively and effectively form amide bonds even if amino acids or peptides with large steric hindrance are used and to thereby produce amide compounds. Further, according to the production method of the present invention, by using a silylating agent and a Lewis acid catalyst, it becomes possible to form amide bonds without using a special activator.

The specific reaction process in the amidation step of the production method of the present invention is unclear, but is inferred as follows. First, it is inferred that the carboxyl group of compound (1) reacts with a silylating agent and is once converted into a silyl ester group, such as a trimethylsilyl ester (refer to the following reaction formula (A)). Next, it is inferred that the silyl ester reacts with the amino group of compound (2) in the presence of a Lewis acid catalyst to form an amide bond (refer to the following reaction formula (B)). It is inferred that the reaction rate of amidation is increased specifically due to weak electron withdrawal of a silyl group. Further, it is inferred that the bond distance between the oxygen atom and the silicon atom is longer than the bond distance between the oxygen atom and the carbon atom, contributing to the reduction in steric hindrance.

[Chem. 4]

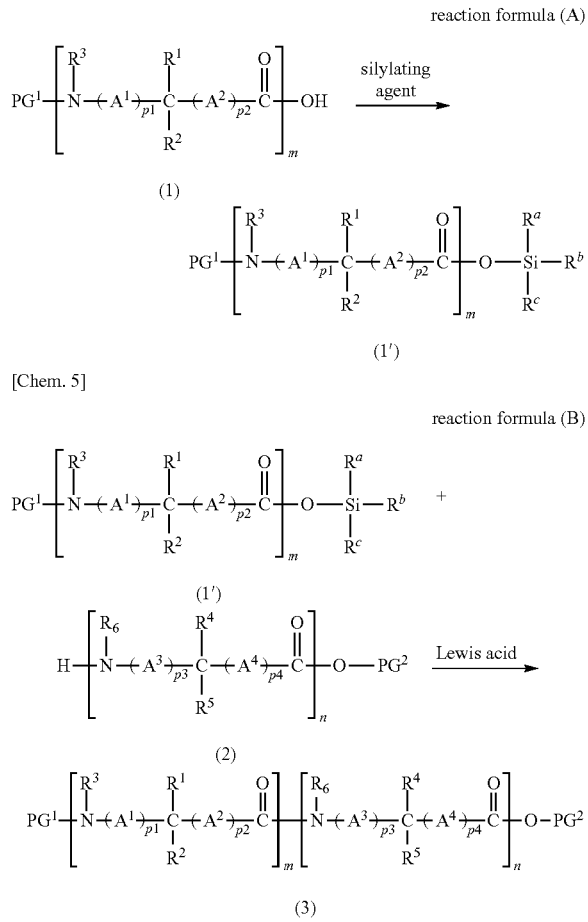

[Chem. 5]

[Chem. 6]

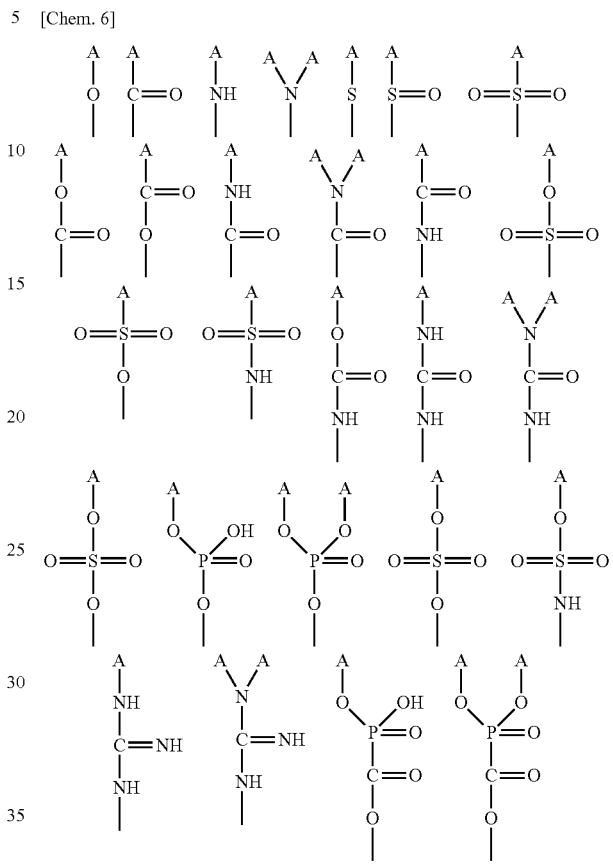

more substituents. When there are two A in one group, they may be the same or different.

In the reaction formulas (A) and (B) above, compound (1') represents a compound obtained by silyl esterification of the carboxyl group of compound (1). In the formulas, a group represented by —Si($R^a$)($R^b$)($R^c$) is a silyl group of a silylating agent. Herein, $R^a$, $R^b$, and $R^c$ each independently represent a hydrogen atom or any substituent (preferably an alkyl group or alkoxy group).

Specific Definition of Each Symbol in General Formulas (1) to (3):

Each group in general formulas (1) to (3) is described below in more detail.

$R^1$, $R^2$, $R^4$, and $R^5$ each independently represent a hydrogen atom, halogen atom, hydroxy group, carboxyl group, nitro group, cyano group, or thiol group, or monovalent hydrocarbon group or heterocyclic group, which may have one, two, or more substituents. When these groups have substituents, the types thereof are the same as above. Specific examples of the number of the substituents include 5, 4, 3, 2, 1, and 0.

When $R^1$, $R^2$, $R^4$, and/or $R^5$ is a monovalent hydrocarbon group or heterocyclic group which may have one, two, or more substituents, there may be linker groups between the hydrocarbon group or heterocyclic group and carbon atoms which bond thereto. The linker groups are each independently selected from, but are not limited to, for example, the following structures. In the following chemical formulas, each A independently represents a monovalent hydrocarbon group or heterocyclic group which may have one, two, or The total number of the carbon atoms of the hydrocarbon group (including its substituents if any) is not particularly limited, but the upper limit thereof is, for example, 20 or lower, 15 or lower, 10 or lower, 8 or lower, or 6 or lower. The lower limit varies depending on the type of hydrocarbon group. The lower limit is 1 or higher in the case of an alkyl group, 2 or higher in the case of an alkenyl group, and 3 or higher, for example, 4 or higher, or 5 or higher in the case of a cycloalkyl group. Specific examples of the number of the atoms include 1, 2, 3, 4, 5, 6, 7, 8, 9, 10, 11, 12, 13, 14, 15, 16, 17, 18, 19, and 20.

The total number of carbon atoms and heteroatoms of the heterocyclic group (including its substituents if any) is not particularly limited, but the upper limit thereof is, for example, 20 or lower, 15 or lower, 10 or lower, 8 or lower, or 6 or lower. The lower limit varies depending on the type of the heterocyclic structure, but is normally 3 or higher, for example, 4 or higher, or 5 or higher. Specific examples of the number of the atoms include 3, 4, 5, 6, 7, 8, 9, 10, 11, 12, 13, 14, 15, 16, 17, 18, 19, and 20.

Specifically, it is preferable that $R^1$, $R^2$, $R^4$, and $R^5$ be each independently a hydrogen atom, hydroxy group, thiol group, carboxyl group, nitro group, cyano group, or halogen atom, or an amino group, alkyl group, alkenyl group, cycloalkyl group, alkoxy group, aryl group, aryloxy group, acyl group, heterocyclic group, or heterocliccoxy group, which may have one, two, or more substituents.

Examples of $R^1$, $R^2$, $R^4$, and $R^5$ include, but are not limited to, for example, the following groups:

a hydrogen atom, hydroxy group, thiol group, carboxyl group, nitro group, and cyano group;
halogen atoms, such as a fluorine atom, chlorine atom, bromine atom, and iodine atom;
alkyl groups, such as a methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;
alkenyl groups, such as an ethenyl group, propenyl group, allyl group, butenyl group, pentenyl group, hexenyl group, heptenyl group, and octenyl group;
alkynyl groups such as a propargyl group;
cycloalkyl groups, such as a cyclopropyl group, cyclobutyl group, cyclopentyl group, cyclohexyl group, cycloheptyl group, bicyclooctyl group, and spirooctyl group;
alkoxy groups, such as a methoxy group, ethoxy group, propoxy group, butoxy group, sec-butoxy group, tert-butoxy group;
aryl groups, such as a phenyl group, benzyl group, tolyl group, naphthyl group, and anthracenyl group;
aryloxy groups, such as a phenyloxy group, benzyloxy group, and naphthyloxy group;
acyl groups, such as an acetyl group, propionyl group, benzoyl group, paramethoxybenzoyl group, and cinnamoyl group;
unsubstituted amino groups and substituted amino groups, such as a dimethylamino group, benzylamino group, and triphenylmethylamino group;
heterocyclic groups, such as a furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydropyridyl group, hexahydropyrimidyl group, hexahydropyridazyl group, 1,2,4,6-tetrahydropyridyl group, 1,2,4,6-tetrahydropyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, and carbazolyl group; and
heterocyclicoxy groups, such as a furanyloxy group, pyrrolyloxy group, indolyloxy group, and quinolyloxy group.

Among the substituents above, substituents having a carboxyl group may or may not have a protecting group. Although reaction selectivity depends on reactivity between compound (1) and compound (2) used in the reaction, the reaction selectivity with the carboxyl group on the right side of the formula of compound (1) is usually improved as compared to the reaction selectivity with the carboxyl group present on a substituent.

$R^3$ and $R^6$ each independently represent a hydrogen atom, carboxyl group, or hydroxy group, or a monovalent hydrocarbon group or heterocyclic group, which may have one, two, or more substituents. When these groups have substituents, the types thereof are the same as above. Specific examples of the number of the substituents include 5, 4, 3, 2, 1, and 0.

When $R^3$ and/or $R^6$ is a monovalent hydrocarbon group or heterocyclic group which may have one, two, or more substituents, there may be linker groups between the hydrocarbon group or heterocyclic group and nitrogen atoms which bond thereto. The linker groups are each independently selected from, but are not limited to, for example, the following structures. In the following chemical formulas, each A independently represents a monovalent hydrocarbon group or heterocyclic group which may have one, two, or more substituents. When there are two A in one group, they may be the same or different.

[Chem. 7]

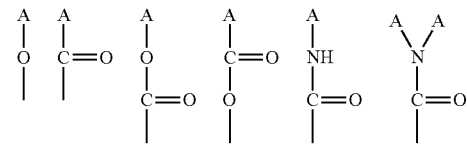

The upper limit of the number of carbon atoms of the hydrocarbon group (including its substituents if any) is, for example, 20 or lower, 15 or lower, 10 or lower, 8 or lower, or 6 or lower. The lower limit varies depending on the type of hydrocarbon group. The lower limit is 1 or higher in the case of an alkyl group, 2 or higher in the case of an alkenyl group or alkynyl group, and 3 or higher, for example, 4 or higher, or 5 or higher in the case of a cycloalkyl group. Specific examples of the number of the atoms include 1, 2, 3, 4, 5, 6, 7, 8, 9, 10, 11, 12, 13, 14, 15, 16, 17, 18, 19, and 20.

The upper limit of the total number of carbon atoms and heteroatoms of the heterocyclic group (including its substituents if any) is, for example, 20 or lower, 15 or lower, 10 or lower, 8 or lower, or 6 or lower. The lower limit varies depending on the type of the heterocyclic structure, but is normally 3 or higher, for example, 4 or higher, or 5 or higher. Specific examples of the number of the atoms include 3, 4, 5, 6, 7, 8, 9, 10, 11, 12, 13, 14, 15, 16, 17, 18, 19, and 20.

Specifically, it is preferable that $R^3$ and $R^6$ be each independently a hydrogen atom, hydroxy group, or carboxyl group, or an alkyl group, alkenyl group, cycloalkyl group, alkoxy group, aryl group, aryloxy group, acyl group, heterocyclic group, or heterocyclicoxy group, which may have one, two, or more substituents.

Examples of $R^3$ and $R^6$ include, but are not limited to, for example, the following groups: a hydrogen atom, hydroxy group, carboxyl group;
alkyl groups, such as a methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;
alkenyl groups, such as an ethenyl group, propenyl group, allyl group, butenyl group, pentenyl group, hexenyl group, heptenyl group, and octenyl group;
alkynyl groups such as a propargyl group;
cycloalkyl groups, such as a cyclopropyl group, cyclobutyl group, cyclopentyl group, cyclohexyl group, cycloheptyl group, bicyclooctyl group, and spirooctyl group;
aryl groups, such as a phenyl group, benzyl group, tolyl group, naphthyl group, and anthracenyl group;
heterocyclic groups, such as a furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydropyridazyl group, hexahydropyrimidyl group, hexahydropyridazyl group, 1,2,4,6-tetrahydropyridyl group, 1,2,4,6-tetrahydropyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, and carbazolyl group.

R and $R^3$ may be bonded together to form, together with a carbon atom to which R bonds and a nitrogen atom to which $R^3$ bonds, a heterocycle which may have one, two, or more substituents. $R^4$ and $R^6$ may be bonded together to form, together with a carbon atom to which $R^4$ bonds and a nitrogen atom to which $R^6$ bonds, a heterocycle which may have one, two, or more substituents. When these groups have substituents, the types thereof are the same as above. Specific examples of the number of the substituents include 5, 4, 3, 2, 1, and 0.

The upper limit of the total number of carbon atoms and heteroatoms of the heterocyclic group (including its substituents if any) is, for example, 20 or lower, 15 or lower, 10 or lower, 8 or lower, or 6 or lower. The lower limit varies depending on the type of the heterocyclic structure, but is normally 3 or higher, for example, 4 or higher, or 5 or higher. Specific examples of the number of the atoms include 3, 4, 5, 6, 7, 8, 9, 10, 11, 12, 13, 14, 15, 16, 17, 18, 19, and 20.

Examples of the heterocyclic group include, but are not limited to, a pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydropyridyl group, hexahydropyrimidyl group, hexahydropyridazyl group, 1,2,4,6-tetrahydropyridyl group, 1,2,4,6-tetrahydropyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5-dihydro-1,3-oxazolyl group, thiazolyl group, 4,5-dihydro-1,3-thiazolyl group, 2,3-dihydro-1,3-thiazolyl group, and 2,5-dihydro-1,3-thiazolyl group.

$A^1$ to $A^4$ each independently represent a divalent aliphatic hydrocarbon group having 1 to 3 carbon atoms, which may have one, two, or more substituents. Specific examples thereof include, but are not limited to, a methylene group, ethylene group, propylene group, and isopropylene group, and these groups are substituted with one, two, or more of the substituents. Specific examples of the number of the substituents include 3, 2, 1, and 0.

p1 to p4 each independently represent 0 or 1.

m and n are each independently an integer of 1 or higher and represent the number of constitutional units represented by a structure in [ ]. Specifically, m represents the number of amino acid units in [ ] of general formula (1). When m is 1, compound (1) is an amino acid. When m is 2 or higher, compound (1) is a peptide. Likewise, n represents the number of amino acid units in [ ] of general formula (2). When n is 1, compound (2) is an amino acid. When n is 2 or higher, compound (2) is a peptide. The upper limit of each of m and n is not particularly limited as long as the amidation step of the production method of the present invention proceeds, but may be, for example, 100 or lower, 80 or lower, 60 or lower, 50 or lower, 40 or lower, 30 or lower, 20 or lower, 15 or lower, 12 or lower, or 10 or lower. For example, m and n may be each independently 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, or 100.

$PG^1$ represents a protecting group of the amino group on the left side of formula (1). The protecting group is not particularly limited as long as the protecting group can protect the amino group during the amidation step and the protected group can be deprotected to the amino group after the reaction.

Various groups are publicly known as the protecting group $PG^1$ of an amino group. Examples thereof include a monovalent hydrocarbon group which may have one, two, or more substituents and a monovalent heterocyclic group which may have one, two, or more substituents. Specifically, a monovalent hydrocarbon group which may have one, two, or more substituents is preferable. There may be a linker group between such a hydrocarbon group or heterocyclic group and the nitrogen atom (to which $PG^1$ bonds in formula (1)) of an amino acid protected thereby. The linker group is not limited. Each linker group is independently selected from, for example, the following linker groups. In the following chemical formulas, each A independently represents a monovalent hydrocarbon group or heterocyclic group which may have one, two, or more substituents. When there are two A in one group, they may be the same or different.

[Chem. 8]

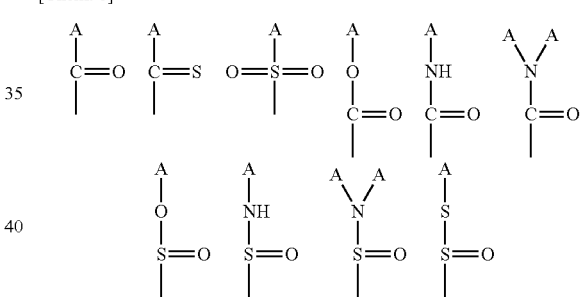

The carbon number of protecting group $PG^1$ is usually 1 or higher or 3 or higher and is usually 20 or lower or 15 or lower.

Specifically, the protecting group $PG^1$ of an amino group is preferably one or more groups selected from a monovalent hydrocarbon group, acyl group, hydrocarbonoxycarbonyl group, hydrocarbon-sulfonyl group, and amide group, which may have one, two, or more substituents.

Specific examples of the protecting group $PG^1$ of an amino group are recited below. The names of amino groups include not only the names of functional groups bonded to the nitrogen atom of an amino group but also the names of groups including the nitrogen atom. Both types of names are included in the following names.

Specific examples of the unsubstituted or substituted hydrocarbon group include: alkyl groups, such as a methyl group, ethyl group, and propyl group; alkenyl groups, such as an ethenyl group, propenyl group, allyl group; alkynyl groups such as a propargyl group; cycloalkyl groups, such as a cyclopropyl group, cyclobutyl group, cyclopentyl group, and cyclohexyl group; aryl groups, such as a phenyl group, benzyl group, paramethoxybenzyl group, tolyl group, and triphenylmethyl group (Troc group); and substituted hydrocarbon groups such as a cyanomethyl group. The carbon number is usually 1 or higher or 3 or higher, and is usually 20 or lower or 15 or lower.

Specific examples of the unsubstituted or substituted acyl group include a benzoyl group (Bz), ortho-methoxybenzoyl group, 2,6-dimethoxybenzoyl group, paramethoxybenzoyl group (PMPCO), cinnamoyl group, and phthaloyl group (Phth).

Specific examples of the unsubstituted or substituted hydrocarbonoxycarbonyl group include a tert-butoxycarbonyl group (Boc), benzyloxycarbonyl group (Cbz), methoxycarbonyl group, ethoxycarbonyl group, 2-trimethylsilylethoxycarbonyl group, 2-phenylethoxycarbonyl group, 1-(1-adamantyl)-1-methylethoxycarbonyl group, 1-(3,5-di-t-butylphenyl)-1-methylethoxycarbonyl group, vinyloxycarbonyl group, allyloxycarbonyl group (Alloc), N-hydroxypiperidinyloxycarbonyl group, p-methoxybenzyloxycarbonyl group, p-nitrobenzyloxycarbonyl group, 2-(1,3-dithianyl)methoxycarbonyl, m-nitrophenoxycarbonyl group, 3,5-dimethoxybenzyloxycarbonyl group, o-nitrobenzyloxycarbonyl group, 2,2,2-trichloroethoxycarbonyl group (Troc), and 9-fluorenylmethyloxycarbonyl group (Fmoc).

Specific examples of the unsubstituted or substituted hydrocarbon-sulfonyl group include a methanesulfonyl group (Ms), toluenesulfonyl group (Ts), and 2- or 4-nitrobenzenesulfonyl group (Ns).

Specific examples of the unsubstituted or substituted amide group include acetamide, o-(benzoyloxymethyl)benzamide, 2-[(t-butyldiphenylsiloxy)methyl]benzamide, 2-toluenesulfonamide, 4-toluenesulfonamide, 2-nitrobenzenesulfonamide, 4-nitrobenzenesulfonamide, tert-butylsulfinylamide, 4-toluenesulfonamide, 2-(trimethylsilyl)ethanesulfonamide, and benzylsulfonamide.

From the viewpoint of deprotection techniques, examples of the protecting group $PG^1$ of an amino group further include protecting groups which can be removed by at least one technique selected from deprotection by hydrogenation, deprotection by weak acid, deprotection by fluorine ion, deprotection by one-electron oxidant, deprotection by hydrazine, and deprotection by oxygen.

Specific preferable examples of the protecting group $PG^1$ of an amino group include a mesyl group (Ms), tert-butoxycarbonyl group (Boc), benzyl group (Bn), benzyloxycarbonyl group (Cbz), benzoyl group (Bz), paramethoxybenzyl group (PMB), 2,2,2-trichloroethoxycarbonyl group (Troc), allyloxycarbonyl group (Alloc), 2,4-dinitrophenyl group (2,4-DNP), phthaloyl group (Phth), paramethoxybenzoyl group (PMPCO), cinnamoyl group, toluenesulfonyl group (Ts), 2- or 4-nitrobenzenesulfonyl group (Ns), cyanomethyl group, and 9-fluorenylmethyloxycarbonyl group (Fmoc). These protecting groups are preferable because they can easily protect an amino group and can be removed under relatively mild conditions, as described above.

Specific more preferable examples of the protecting group $PG^1$ of an amino group include a mesyl group (Ms), tert-butoxycarbonyl group (Boc), benzyloxycarbonyl group (Cbz), benzyl group (Bn), paramethoxybenzyl group (PMB), 2,2,2-trichloroethoxycarbonyl group (Troc), allyloxycarbonyl group (Alloc), paramethoxybenzoyl group (PMPCO), benzoyl group (Bz), cyanomethyl group, cinnamoyl group, 2- or 4-nitrobenzenesulfonyl group (Ns), toluenesulfonyl group (Ts), phthaloyl group (Phth), 2,4-dinitrophenyl group (2,4-DNP), and 9-fluorenylmethyloxycarbonyl group (Fmoc).

Specific further more preferable examples of the protecting group $PG^1$ of an amino group include a mesyl group (Ms), tert-butoxycarbonyl group (Boc), benzyloxycarbonyl group (Cbz), benzyl group (Bn), paramethoxybenzyl group (PMB), 2,2,2-trichloroethoxycarbonyl group (Troc), allyloxycarbonyl group (Alloc), paramethoxybenzoyl group (PMPCO), benzoyl group (Bz), cyanomethyl group, and cinnamoyl group.

$PG^2$ represents a protecting group of the carboxyl group on the right side of formula (2). The protecting group is not particularly limited as long as the protecting group can protect the carboxyl group during the amidation step and the protected group can be deprotected to the carboxyl group after the reaction.

Examples of the protecting group $PG^2$ of a carboxyl group include a monovalent hydrocarbon group and heterocyclic group which may have one, two, or more substituents. When these groups have substituents, the types thereof are the same as above. Specific examples of the number of the substituents include 5, 4, 3, 2, 1, and 0.

The upper limit of the number of carbon atoms of the hydrocarbon group (including its substituents if any) is, for example, 20 or lower, 15 or lower, 10 or lower, 8 or lower, or 6 or lower. The lower limit varies depending on the type of hydrocarbon group. The lower limit is 1 or higher in the case of an alkyl group, 2 or higher in the case of an alkenyl group or alkynyl group, and 3 or higher, for example, 4 or higher, or 5 or higher in the case of a cycloalkyl group. Specific examples of the number of the atoms include 1, 2, 3, 4, 5, 6, 7, 8, 9, 10, 11, 12, 13, 14, 15, 16, 17, 18, 19, and 20.

The upper limit of the total number of carbon atoms and heteroatoms of the heterocyclic group (including its substituents if any) is, for example, 20 or lower, 15 or lower, 10 or lower, 8 or lower, or 6 or lower. The lower limit varies depending on the type of the heterocyclic structure, but is normally 3 or higher, for example, 4 or higher, or 5 or higher. Specific examples of the number of the atoms include 3, 4, 5, 6, 7, 8, 9, 10, 11, 12, 13, 14, 15, 16, 17, 18, 19, and 20.

Examples of the protecting group $PG^2$ of a carboxyl group include, but are not limited to, for example, the following groups:

alkyl groups, such as a methyl group, ethyl group, propyl group, isopropyl group, n-butyl group, isobutyl group, tert-butyl group, sec-butyl group, pentyl group, isopentyl group, neopentyl group, hexyl group, heptyl group, octyl group, decyl group, and nonyl group;

alkenyl groups, such as an ethenyl group, propenyl group, allyl group, butenyl group, pentenyl group, hexenyl group, heptenyl group, and octenyl group;

alkynyl groups such as a propargyl group;

cycloalkyl groups, such as a cyclopropyl group, cyclobutyl group, cyclopentyl group, cyclohexyl group, cycloheptyl group, bicyclooctyl group, and spirooctyl group;

aryl groups, such as a phenyl group, benzyl group, tolyl group, naphthyl group, and anthracenyl group;

heterocyclic groups, such as a furanyl group, thiophenyl group, pyranyl group, pyrrolinyl group, pyrrolyl group, 2,3-dihydro-1H-pyrrolyl group, piperidinyl group, piperazinyl group, homopiperazinyl group, morpholino group, thiomorpholino group, 1,2,4,6-tetrahydropyridyl group, hexahydropyrimidyl group, hexahydropyridazyl group, 1,2,4,6-tetrahydropyridyl group, 1,2,4,6-tetrahydropyridazyl group, 3,4-dihydropyridyl group, imidazolyl group, 4,5-dihydro-1H-imidazolyl group, 2,3-dihydro-1H-imidazolyl group, pyrazolyl group, 4,5-dihydro-1H-pyrazolyl group, 2,3-dihydro-1H-pyrazolyl group, oxazolyl group, 4,5-dihydro-1,3-oxazolyl group, 2,3-dihydro-1,3-oxazolyl group, 2,5- dihydro-1,3-oxazolyl group, thiazolyl group, 4,5-dihydro-1,3-thiazolyl group, 2,3-dihydro-1,3-thiazolyl group, 2,5-dihydro-1,3-thiazolyl group, and carbazolyl group.

In compound (2), the amino group on the left side of general formula (2) may form a salt with another acid. Examples thereof include, but are not limited to, aliphatic carboxylic acids having 1 to 5 carbon atoms, such as acetic acid and propionic acid; and trifluoroacetic acid, hydrochloric acid, hydrobromic acid, sulfuric acid, nitric acid, phosphoric acid, boric acid, and sulfonic acid.

Amount Ratio of Compound (1) and Compound (2):

The amount ratio of compound (1) and compound (2) used in the production method of the present invention is not particularly limited. With respect to 1 mol of compound (1), compound (2) is used in the range of usually 0.1 mol or more, for example, 0.2 mol or more, 0.3 mol or more, or 0.5 mol or more, and usually 20 mol or less, for example, 10 mol or less, 8 mol or less, 6 mol or less, 5 mol or less, or preferably 2 mol or less.

It is preferable to use more of compound (1) than compound (2) because the reaction efficiency is high. Specifically, the molar ratio of compound (2) with respect to 1 mol of compound (1) is preferably 0.5 or less.

Lewis Acid Catalyst:

The type of Lewis acid catalyst used in the production method of the present invention is not limited as long as the Lewis acid compound can induce amidation between the carboxyl group of compound (1) and the amino group of compound (2) in the presence of the undermentioned silylating agent. Specifically, the Lewis acid catalyst is preferably a metal compound that functions as a Lewis acid.

Examples of a metal element constituting the metal compound include various metals belonging to groups 2 to 15 of the Periodic Table of the Elements. Specific examples of the metal element include boron, magnesium, aluminum, gallium, indium, silicon, calcium, lead, bismuth, mercury, transition metals, and lanthanoid elements. Specific examples of the transition metals include scandium, titanium, vanadium, chromium, manganese, iron, cobalt, nickel, copper, zinc, yttrium, zirconium, niobium, molybdenum, technetium, ruthenium, rhodium, palladium, tin, silver, cadmium, hafnium, tantalum, tungsten, rhenium, osmium, iridium, platinum, gold, and thallium. Specific examples of the lanthanoid elements include lanthanum, cerium, neodymium, samarium, europium, gadolinium, holmium, erbium, thulium, and ytterbium. Thereamong, from the viewpoint that an excellent reaction promoting effect is exhibited and an amide compound is produced with high stereoselectivity, one, two, or more selected from titanium, zirconium, hafnium, tantalum, niobium, boron, vanadium, tungsten, neodymium, iron, lead, cobalt, copper, silver, palladium, tin, and thallium are preferable. One, two, or more selected from titanium, zirconium, hafnium, tantalum, and niobium are preferable. One, two, or more metal elements may be contained in the metal compound. When two or more metal elements are contained in the metal compound, the types thereof may be the same or different.

A ligand constituting the metal compound can be appropriately selected in accordance with the type of metal. Specific examples of the ligand include: substituted or unsubstituted, linear or branched alkoxy groups having 1 to 10 carbon atoms, such as a methoxy group, ethoxy group, propoxy group, butoxy group, trifluoroethoxy group, and trichloroethoxy group; halogen atoms, such as a fluorine atom, chlorine atom, bromine atom, and iodine atom; allyloxy groups having 1 to 10 carbon atoms; an acetylacetonate group (acac), acetoxy group (AcO), trifluoromethanesulfonate group (TfO); substituted or unsubstituted, linear or branched alkyl groups having 1 to 10 carbon atoms; a phenyl group, oxygen atom, sulfur atom, group —SR (where R is a substituent which may be a substituted or unsubstituted hydrocarbon group having about 1 to 20 carbon atoms), group —NRR' (where R and R' are each independently a hydrogen atom or a substituent which may be a substituted or unsubstituted hydrocarbon group having about 1 to 20 carbon atoms), and cyclopentadienyl (Cp) group.

Specifically, the metal compound is preferably a titanium compound, zirconium compound, hafnium compound, tantalum compound, or niobium compound. Specific examples of each compound are described below.

Specific examples of the titanium compound include a compound represented by $TiX^1_4$ (where four $X^1$ are each independently the ligand above and the four $X^1$ may be the same or different). When $X^1$ is an alkoxy group, the alkoxy group is preferably a linear or branched alkoxy group having 1 to 10 carbon atoms, specifically a linear or branched alkoxy group having 1 to 5 carbon atoms, or more specifically a linear or branched alkoxy group having 1 to 4 carbon atoms. When $X^1$ is an allyloxy group, the allyloxy group is preferably an allyloxy group having 1 to 20 carbon atoms, specifically an allyloxy group having 1 to 15 carbon atoms, or more specifically an allyloxy group having 1 to 10 carbon atoms. These ligands may have additional substituents. When $X^1$ is a halogen atom, the halogen atom is preferably a chlorine atom or bromine atom. Specifically, for example, $Ti(OMe)_4$, $Ti(OEt)_4$, $Ti(OPr)_4$, $Ti(Oi-Pr)_4$, $Ti(OBu)_4$, $Ti(Ot-Bu)_4$, $Ti(OCH_2CH(Et)Bu)_4$, $CpTiCl_3$, $Cp_2TiCl_2$, $Cp_2Ti(OTf)_2$, $(i-PrO)_2TiCl_2$, and $(i-PrO)_3TiCl$ are preferable.

Specific examples of the zirconium compound include a compound represented by $ZrX^2_4$ (where four $X^2$ are each independently the ligand above and the four $X^2$ may be the same or different). When $X^2$ is an alkoxy group, the alkoxy group is preferably a linear or branched alkoxy group having 1 to 10 carbon atoms, specifically a linear or branched alkoxy group having 1 to 5 carbon atoms, or more specifically a linear or branched alkoxy group having 1 to 4 carbon atoms. When $X^2$ is an allyloxy group, the allyloxy group is preferably an allyloxy group having 1 to 20 carbon atoms, specifically an allyloxy group having 1 to 15 carbon atoms, or more specifically an allyloxy group having 1 to 10 carbon atoms. These ligands may have additional substituents. When $X^2$ is a halogen atom, the halogen atom is preferably a chlorine atom or bromine atom. Specifically, for example, $Zr(OMe)_4$, $Zr(OEt)_4$, $Zr(OPr)_4$, $Zr(Oi-Pr)_4$, $Zr(OBu)_4$, $Zr(Ot-Bu)_4$, $Zr(OCH_2CH(Et)Bu)_4$, $CpZrCl_3$, $Cp_2ZrCl_2$, $Cp_2Zr(OTf)_2$, $(i-PrO)_2ZrCl_2$, and $(i-PrO)_3ZrCl$ are preferable.

Specific examples of the hafnium compound include a compound represented by $HfX^3_4$ (where four $X^3$ are each independently the ligand above and the four $X^3$ may be the same or different). When $X^3$ is an alkoxy group, the alkoxy group is preferably a linear or branched alkoxy group having 1 to 10 carbon atoms, specifically a linear or branched alkoxy group having 1 to 5 carbon atoms, or more specifically a linear or branched alkoxy group having 1 to 4 carbon atoms. When $X^3$ is an allyloxy group, the allyloxy group is preferably an allyloxy group having 1 to 20 carbon atoms, specifically an allyloxy group having 1 to 15 carbon atoms, or more specifically an allyloxy group having 1 to 10 carbon atoms. These ligands may have additional substituents. When $X^3$ is a halogen atom, the halogen atom is preferably a chlorine atom or bromine atom. Specifically, for example, $HfCp_2Cl_2$, $HfCpCl_3$, and $HfCl_4$ are preferable.

Specific examples of the tantalum compound include a compound represented by $TaX^4{}_5$ (where five $X^4$ are each independently the ligand above and the five $X^4$ may be the same or different). When $X^4$ is an alkoxy group, the alkoxy group is preferably a linear or branched alkoxy group having 1 to 10 carbon atoms, specifically a linear or branched alkoxy group having 1 to 5 carbon atoms, or more specifically a linear or branched alkoxy group having 1 to 3 carbon atoms. When $X^4$ is an allyloxy group, the allyloxy group is preferably an allyloxy group having 1 to 20 carbon atoms, specifically an allyloxy group having 1 to 15 carbon atoms, or more specifically an allyloxy group having 1 to 10 carbon atoms. These ligands may have additional substituents. When $X^4$ is a halogen atom, the halogen atom is preferably a chlorine atom or bromine atom. Specifically, a tantalum alkoxide compound (for example, $X^4$ is an alkoxy group) is preferable. For example, $Ta(OMe)_5$, $Ta(OEt)_5$, $Ta(OBu)_5$, $Ta(NMe_2)_5$, $Ta(acac)(OEt)_4$, $TaCl_5$, $TaCl_4(THF)$, and $TaBr_5$ are preferable. A compound in which $X^4$ is oxygen, i.e., $Ta_2O_5$, can be used.

Specific examples of the niobium compound include a compound represented by $NbX^5{}_5$ (where five $X^5$ are each independently the ligand above and the five $X^5$ may be the same or different). When $X^5$ is an alkoxy group, the alkoxy group is preferably a linear or branched alkoxy group having 1 to 10 carbon atoms, specifically a linear or branched alkoxy group having 1 to 5 carbon atoms, or more specifically a linear or branched alkoxy group having 1 to 3 carbon atoms. When $X^5$ is an allyloxy group, the allyloxy group is preferably an allyloxy group having 1 to 20 carbon atoms, specifically an allyloxy group having 1 to 15 carbon atoms, or more specifically an allyloxy group having 1 to 10 carbon atoms. These ligands may have additional substituents. When $X^5$ is a halogen atom, the halogen atom is preferably a chlorine atom or bromine atom. Specifically, a tantalum alkoxide compound (for example, $X^5$ is an alkoxy group) is preferable. For example, $NbCl_4(THF)$, $NbCl_5$, $Nb(OMe)_5$, and $Nb(OEt)_5$ are preferable. A compound in which $X^5$ is oxygen, i.e., $Nb_2O_5$, can be used.

The preferable metal compound as the Lewis acid catalyst in the production method of the present invention varies depending on the types of compound (1) and compound (2).

When compound (1) and compound (2) are each an amino acid (i.e., when m and n are each 1), the Lewis acid catalyst is preferably a tantalum compound or a niobium compound.

However, when either or both of compound (1) and compound (2) are peptides (i.e., when either or both of m and n are 2 or more), the Lewis acid catalyst is preferably a titanium compound, zirconium compound, or hafnium compound, and specifically preferably a titanium compound. Although the reason therefor is unclear, it is inferred that titanium metal has a small atomic radius whereby a titanium catalyst is suitable for activation on a 7-membered ring and thus less influenced by steric hindrance of a peptide chain.

Any one of the Lewis acid catalysts may be used alone and two or more of the Lewis acid catalysts may be used in any combination.

The amount of the Lewis acid catalyst used is not particularly limited as long as the amount is enough for inducing amidation between the carboxyl group of compound (1) and the amino group of compound (2) in the presence of the undermentioned silylating agent. For example, the amount of the Lewis acid catalyst used is usually 0.1 mol % or more, preferably, for example, 0.2 mol % or more, or 0.3 mol % or more, and usually 30 mol % or less, for example, 20 mol % or less, or 15 mol % or less with respect to 100 mol % of compound (1) or compound (2).

The Lewis acid catalyst may be supported by a carrier. The carrier supporting the Lewis acid catalyst is not particularly limited and can be any of publicly known carriers. The method for making the carrier support the Lewis acid catalyst can be any of publicly known methods.

Silylating Agent:

The type of silylating agent used in the production method of the present invention is not limited as long as the silylating agent can induce amidation between the carboxyl group of compound (1) and the amino group of compound (2) in the presence of the undermentioned Lewis acid catalyst.

As described above, it is inferred that the silylating agent converts the carboxyl group of compound (1) into a silyl ester, such as trimethylsilyl, whereby amidation with high stereoselectivity is possible. Thus, the silylating agent is preferably a silicon-containing compound having ability to convert a carboxyl group to a silyl ester. When a carboxy group and an amino group coexist, it is preferable that the silylating agent reacts selectively with the carboxyl group.

Examples of the silylating agent include, but are not limited to, a silylimidazole compound represented by the following general formula (4-1), a silyltriazole compound represented by the following general formula (4-2), a silylhalide compound represented by the following general formula (4-3), a silylamide compound represented by the following general formula (4-4), and a silylamine compound represented by the following general formula (4-5).

[Chem. 9]

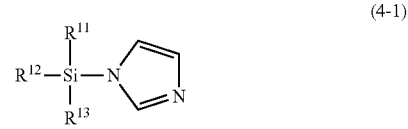

(4-1)

[Chem. 10]

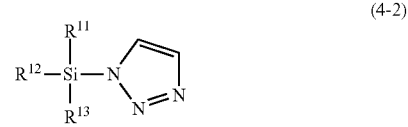

(4-2)

[Chem. 11]

(4-3)

[Chem. 12]

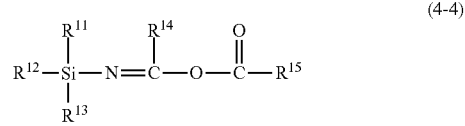

(4-4)

[Chem. 13]

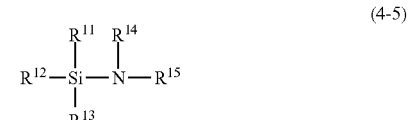

(4-5)

In the formulas, $R^{11}$ to $R^{15}$ are each independently an optionally substituted linear or branched alkyl group or alkoxy group having 1 to 10 carbon atoms (preferably 1 to 5, specifically 1 to 3 carbon atoms).

In the formulas, X represents a halogen group, such as chlorine atom or bromine atom.

Examples of the silylimidazole compound represented by general formula (4-1) include 1-(trimethylsilyl)imidazole (TMSIM) and 1-(tert-butyldimethylsilyl)imidazole (TBSIM). Specifically, TMSIM and TBSIM are particularly preferable.

Examples of the silyltriazole compound represented by general formula (4-2) include 1-(trimethylsilyl)triazole and 1-(tert-butyldimethylsilyl)triazole.

Examples of the silylhalide compound represented by general formula (4-3) include trimethylbromosilane (TMBS) and trimethylchlorosilane (TMCS). Specifically, TMBS is particularly preferable.

Examples of the silylamide compound represented by general formula (4-4) include N-methyl-N-(trimethylsilyl)trifluoroacetamide (MSTFA), N,O-bis(trimethylsilyl)trifluoroacetamide (BSTFA), and N,O-bis(trimethylsilyl)acetamide (BSA). Specifically, MSTFA is particularly preferable.

Examples of the silylamine compound represented by general formula (4-5) include N-(trimethylsilyl)dimethylamine (TMSDMA) and hexamethyldisilazane (HMDS). Specifically, TMSDMA is particularly preferable.

Specifically, the silylating agent is preferably a silylimidazole compound, more preferably a trialkylsilylimidazole compound or trialkoxysilylimidazole compound.

Any one of the silylating agents may be used alone and two or more of the silylating agents may be used in any combination.

The amount of the silylating agent used is not particularly limited as long as the amount is enough for inducing amidation between the carboxyl group of compound (1) and the amino group of compound (2) in the presence of the undermentioned Lewis acid catalyst. For example, the amount of the silylating agent used is usually 0.1 mol or more, for example, 0.2 mol or more, 0.3 mol or more, or 0.5 mol or more with respect to 1 mol of compound (1). Specifically, 1 mol or more of the silylating agent with respect to 1 mol of compound (1) is preferably used. The upper limit of the amount of the silylating agent used is not particularly limited. The amount thereof used is usually in a range of 20 mol or less, for example, 10 mol or less, 8 mol or less, 6 mol or less, or 5 mol or less with respect to 1 mol of compound (1). The amount thereof used is preferably 2 mol or less in terms of reaction efficiency.

Other Components:

When the amidation is carried out in the production method of the present invention, the compound (1), compound (2), Lewis acid catalyst, and silylating agent may coexist with other components.

For example, amidation may be carried out in the presence of a base from the viewpoint of increasing reaction efficiency. The base is not particularly limited. Examples thereof include amines having 1 to 3 linear or branched alkyl groups each having 1 to 10 carbon atoms, such as triethylamine ($Et_3N$), diisopropylamine (i-$Pr_2NH$), and diisopropylethylamine (i-$Pr_2EtN$). The amount of the base used is not particularly limited. The amount of the base is preferably about 20 to 120 mol % with respect to 100 mol % of compound (1) or compound (2), and more preferably about 50 to 100 mol %.

The amidation may be carried out in the presence of a ligand. The ligand is not particularly limited. Examples thereof include 2,2'-bipyridine, 8-hydroxyquinoline, [2,2'-bisquinoline]-8,8'-diol, and 2,2':6',2":6"',2'"-quarterpyridine. The metal coordination form of a metal compound used as the catalyst varies depending on the position of a heteroatom of the ligand. Thus, amidation proceeds at various distances. The amount of the ligand used is not particularly limited. The amount of the ligand is preferably 20 mol % or less with respect to 100 mol % of compound (1) or compound (2) and is more preferably about 0.1 mol % to 10 mol %.

Reaction Procedures:

The amidation of the production method of the present invention can be carried out by contacting compound (1), compound (2), a Lewis acid catalyst, a silylating agent, and optionally other components. The sequence of the contact is not particularly limited. All may be mixed simultaneously or sequentially in any order.

Specifically, in the production method of the present invention, it is considered that compound (1) and a silylating agent usually react to form a silyl ester (1') of compound (1) (refer to the reaction formula (A)). It is considered that the thus-formed silyl ester (1') is contacted to compound (2) in the presence of a Lewis acid catalyst, resulting in amidation (refer to the reaction formula (B)).

In the above inferred reaction mechanism of the production method of the present invention, for example, it is admissible that the compound (1) and the silylating agent react to form a silyl ester (1') of compound (1), and thereafter, the compound (2) and Lewis acid are added and contacted thereto. The silylating agent, even in coexistence with a carboxyl group and an amino group, usually reacts selectively with the carboxyl group, and does not inhibit the subsequent amidation, and thus, all the reaction components may be mixed simultaneously. In terms of reaction efficiency, it is preferable to carry out the reaction by mixing all simultaneously.

From the viewpoint of increasing reaction efficiency, amidation may be carried out in an organic solvent. The organic solvent is not particularly limited. Examples thereof include aromatic hydrocarbons, such as toluene and xylene; ethers, such as pentane, petroleum ether, 1-methyltetrahydrofuran (1-MeTHF), diisopropyl ether (i-$Pr_2O$), diethylether ($Et_2O$), and cyclopentyl methyl ether (CPME); esters, such as ethyl acetate (AcOEt); and organic acids, such as acetic acid. Any one of organic solvents may be used alone and two or more of organic solvents may be used in any combination.

The concentrations of compound (1) and compound (2) in a reaction system are not particularly limited. From the viewpoint of increasing reaction efficiency, the concentrations are preferably 2 vol % to 70 vol %.

Reaction Conditions:

The reaction conditions of the amidation of the production method of the present invention are as follows:

The reaction temperature is not limited as long as the amidation between the carboxyl group of compound (1) and the amino group of compound (2) proceeds in coexistence of a silylating agent and a Lewis acid catalyst. It is preferable that the temperature be usually 0° C. or higher, particularly 10° C. or higher, specifically 20° C. or higher, and usually 100° C. or lower, particularly 80° C. or lower, specifically 60° C. or lower. Specifically, the production method of the present invention is advantageous since amidation proceeds sufficiently under mild conditions, such as 60° C. or lower.

The reaction temperature is not limited as long as the amidation between the carboxyl group of compound (1) and the amino group of compound (2) proceeds in coexistence of a silylating agent and a Lewis acid catalyst. The reaction may be carried out under any of reduced pressure, normal pressure, or increased pressure. It is usually preferable to carry out the reaction at normal pressure.

The reaction atmosphere is not limited as long as the amidation between the carboxyl group of compound (1) and the amino group of compound (2) proceeds in coexistence of a silylating agent and a Lewis acid catalyst. It is preferable to carry out the reaction under an atmosphere of an inert gas such as argon or nitrogen.

The reaction time is not limited as long as the amidation between the carboxyl group of compound (1) and the amino group of compound (2) proceeds in coexistence of a silylating agent and a Lewis acid catalyst. From the viewpoint of proceeding the reaction sufficiently and efficiently, it is preferable to carry out the reaction for, for example, 10 minutes or more, particularly 20 minutes or more, or 30 minutes or more, and, for example, 80 hours or less, particularly 60 hours or less, or 50 hours or less.

Post-Treatment (Purification/Collection):

In the production method of the present invention, the compound (3) generated by amidation may be subjected to various post-treatments.

For example, the generated compound (3) can be isolated/purified by a conventional method, such as column chromatography or recrystallization.

After the compound (3) is optionally isolated/purified, the amino group protected by $PG^1$ and/or the carboxyl group protected by $PG^2$ can be deprotected.

The method for deprotection of the amino group protected by $PG^1$ is not limited. Various methods can be used depending on the type of protecting group $PG^1$. Examples thereof include deprotection by hydrogenation, deprotection by weak acid, deprotection by fluorine ion, deprotection by one-electron oxidant, deprotection by hydrazine, and deprotection by oxygen. Examples of the deprotection by hydrogenation include (a) a deprotection method via reduction using a metal catalyst, such as palladium, palladium-carbon, palladium hydroxide, or palladium hydroxide-carbon, as a reduction catalyst in the presence of hydrogen gas and (b) a deprotection method via reduction using a hydrogenation reducing agent, such as sodium borohydride, lithium aluminum hydride, lithium borohydride, or diborane in the presence of a metal catalyst, such as palladium, palladium-carbon, palladium hydroxide, or palladium hydroxide-carbon.

The method for deprotection of the amino group protected by $PG^2$ is not limited. Various methods can be used depending on the type of protecting group $PG^2$. Examples thereof include deprotection by hydrogenation, deprotection by base, and deprotection by weak acid. Examples of the deprotection by base include a deprotection method using a strong base, such as lithium hydroxide, sodium hydroxide, or potassium hydroxide as the base.

After the amidation of the production method of the present invention is carried out, the amino group protected by $PG^1$ or the carboxyl group protected by $PG^2$ of the obtained compound (3) is deprotected, this compound is subjected as new compound (1) or (2) to the production method of the present invention to be linked to another compound (2) or (1) via an amide bond. By repeating the production method of the present invention in this manner, it is possible, in principle, to synthesize peptides with any amino acid sequences.

Alternatively, after the amidation of the production method of the present invention is carried out, a different amino acid can be further bonded to the obtained compound (3) by another method. Examples of this method include the method described in international patent application PCT/JP2018/016767 filed by the present inventors. The method described in PCT/JP2018/016767 comprises forming an amide bond between a carboxyl group of a first amino acid or peptide and an amino group of a second amino acid in the presence of a metal catalyst such as a specific tantalum compound or niobium compound. Specifically, the protecting group $PG^2$ of a carboxyl group of compound (2) is preliminarily formed into a protecting group which is reactive in the presence of the metal catalyst, such as a specific tantalum compound or niobium compound, used in the method described in PCT/JP2018/016767, compound (3) is produced by the production method of the present invention, and a different amino acid is reacted with and linked by amidation to the compound (3) by the method described in PCT/JP2018/016767.

EXAMPLES

The present invention will be described in detail with reference to the Examples. However, the present invention is not limited thereto and can be carried out in any embodiment without departing from the scope of the present invention.

Amide compounds were produced according to the production method of the present invention as described in the following Examples.

In the following Examples, the diastereomer ratio and the enantiomer ratio were determined by $^1$H-NMR analysis under the following conditions. However, only in Example 4, they were determined by HPLC analysis under the following conditions.

[Analysis Conditions]

$^1$H-NMR:

Measuring device: JEOL 400SS manufactured by JEOL Ltd.
Measurement conditions: 400 MHz
Measurement solvent: $CDCl_3$ (or $CD_3OD$ only in Example 28)

$^{29}$Si-NMR (Measured Only in Reference Examples 1 and 2):

Measuring device: JEOL 400SS manufactured by JEOL Ltd.
Measurement conditions: 80 MHz
Measurement solvent: $CDCl_3$ High-Speed Liquid Chromatograph (HPLC):
Device name: CBM 20A manufactured by Shimadzu Corp.
Detector: SPD-M20A manufactured by Shimadzu Corp.
Column: IA-3 (φ4.6 mm×25 cm) manufactured by Daicel Corp.
Eluent: 2-propanol/n-hexane=2/98 (vol/vol)
Detection wavelength: λ=216 nm Example Group 1: Production of an Amide Compound Via Amidation of Two α-Amino Acids Example 1-1: Production of Boc-L-Asp(L-Ala-Ot-Bu)-Ot-Bu L-Ala-Ot-Bu-HCl (manufactured by Watanabe Chemical Industries, Ltd.) was neutralized using Amberlyst A21 free amine (manufactured by Sigma-Aldrich Co.) to obtain L-Ala-Ot-Bu.

In a glove box under an argon atmosphere, Boc-L-Asp(OH)-Ot-Bu (manufactured by Watanabe Chemical Industries, Ltd., 578.6 mg, 2.0 mmol), the L-Ala-Ot-Bu (145.2 mg, 1.0 mmol), 1-(trimethylsilyl)imidazole (manufactured by Tokyo Chemical Industry Co., Ltd., 308.6 mg, 2.2 mmol), and Ta(OMe)$_5$ (manufactured by Sigma-Aldrich Co., 33.6 mg, 0.10 mmol) together with a stirrer were put into a dried 5-mL screw vial, which was covered with a screw cap and sealed under the argon atmosphere. This screw vial was removed from the glove box and placed in an oil bath. After stirring at a reaction temperature of 50° C. for 72 hours, the screw vial was removed and allowed to cool to ambient temperature. The reaction product obtained in the screw vial was diluted with chloroform (manufactured by Wako Chemical Co., Ltd., 15 mL) and purified by flash silica gel column chromatography (ethyl acetate/n-hexane). Thereafter, the solvent was removed by distillation using an evaporator, whereby a white solid of Boc-L-Asp(L-Ala-Ot-Bu)-Ot-Bu (393.0 mg) was obtained. The yield was 94% and the diastereomeric ratio was >99:1.

Example 1-2: Production of Boc-L-Lys(Boc)-L-Ala-Ot-Bu

Boc-L-Lys(Boc)-L-Ala-Ot-Bu (424.8 mg) was synthesized and obtained by the same procedures as in Example 1-1 except for Boc-L-Lys(Boc)-OH (manufactured by Watanabe Chemical Industries, Ltd., 692.8 mg, 2.0 mmol) in place of the Boc-L-Asp(OH)-Ot-Bu of Example 1-1. The yield was 90% and the diastereomer ratio was >99:1.

Example 1-3: Production of Boc-L-Pro-L-Ala-Ot-Bu

Boc-L-Pro-L-Ala-Ot-Bu (341.4 mg) was synthesized and obtained by the same procedures as in Example 1-1 except for Boc-L-Pro-OH (manufactured by Watanabe Chemical Industries, Ltd., 430.5 mg, 2.0 mmol) in place of the Boc-L-Asp(OH)-Ot-Bu of Example 1-1. The yield was 99% and the diastereomer ratio was >99:1.

Example 1-4: Production of Boc-L-Ala-Gly-Ot-Bu

Boc-L-Ala-OH (manufactured by Watanabe Chemical Industries, Ltd., 378.4 mg, 2.0 mmol), Gly-Ot-Bu (manufactured by Combi-Blocks, Inc., 131.2 mg, 1.0 mmol), 1-(trimethylsilyl)imidazole (308.6 mg, 2.2 mmol), and Ta(OMe)$_5$ (33.6 mg, 0.10 mmol) were put into a screw vial, which was covered with a screw cap and sealed under an argon atmosphere by the same procedures as in Example 1-1. Via the same reaction as in Example 1-1, a white solid of Boc-L-Ala-Gly-Ot-Bu (290.5 mg) was obtained. The yield was 96% and the enantiomer ratio was >99:1.

Example 1-5: Production of Boc-L-Ala-L-Trp(Boc)-Ot-Bu

L-Trp(Boc)-Ot-Bu-HCl (manufactured by Watanabe Chemical Industries, Ltd.) was neutralized with Amberlyst A21 free amine to obtain L-Trp(Boc)-Ot-Bu.
A white solid of Boc-L-Ala-L-Trp(Boc)-Ot-Bu (486.1 mg) was obtained by the same method as in Example 1-4 except for the L-Trp(Boc)-Ot-Bu (360.5 mg, 1.0 mmol) in place of the Gly-Ot-Bu of Example 1-4. The yield was 91% and the diastereomeric ratio was >99:1.

Example 1-6: Production of Boc-L-Ala-L-Asp(t-Bu)-Ot-Bu

L-Asp(t-Bu)-Ot-Bu-HCl (manufactured by Watanabe Chemical Industries, Ltd.) was neutralized with Amberlyst A21 free amine to obtain L-Asp(t-Bu)-Ot-Bu.
A white solid of Boc-L-Ala-L-Asp(t-Bu)-Ot-Bu (415.9 mg) was obtained by the same method as in Example 1-4 except for the L-Asp(t-Bu)-Ot-Bu (245.3 mg, 1.0 mmol) in place of the Gly-Ot-Bu of Example 1-4. The yield was 99% and the diastereomeric ratio was >99:1.

Example 1-7: Production of Boc-L-Ala-L-Cys(Trt)-Ot-Bu

L-Cys(Trt)-Ot-Bu-HCl (manufactured by Watanabe Chemical Industries, Ltd.) was neutralized with Amberlyst A21 free amine to obtain L-Cys(Trt)-Ot-Bu.
A white solid of Boc-L-Ala-L-Cys(Trt)-Ot-Bu (585.0 mg) was obtained by the same method as in Example 1-4 except for the L-Cys(Trt)-Ot-Bu (419.5 mg, 1.0 mmol) in place of the Gly-Ot-Bu of Example 1-4. The yield was 99% and the diastereomeric ratio was >99:1.

Example 1-8: Production of Boc-L-Ala-L-Lys(Boc)-Ot-Bu

L-Lys(Boc)-Ot-Bu-HCl (manufactured by Watanabe Chemical Industries, Ltd.) was neutralized with Amberlyst A21 free amine to obtain L-Lys(Boc)-Ot-Bu.
A white solid of Boc-L-Ala-L-Lys(Boc)-Ot-Bu (462.1 mg) was obtained by the same method as in Example 1-4 except for the L-Lys(Boc)-Ot-Bu (302.4 mg, 1.0 mmol) in place of the Gly-Ot-Bu of Example 1-4. The yield was 98% and the diastereomeric ratio was >99:1.

Example 1-9: Production of Boc-L-Ala-L-Arg(Mtr)-Ot-Bu

L-Arg(Mtr)-Ot-Bu-HCl (manufactured by Watanabe Chemical Industries, Ltd.) was neutralized with Amberlyst A21 free amine to obtain L-Arg(Mtr)-Ot-Bu.
A white solid of Boc-L-Ala-L-Arg(Mtr)-Ot-Bu (530.6 mg) was obtained by the same method as in Example 1-4 except for the L-Arg(Mtr)-Ot-Bu (442.6 mg, 1.0 mmol) in place of the Gly-Ot-Bu of Example 1-4. The yield was 86% and the diastereomeric ratio was >99:1.

Example 1-10: Production of Boc-L-Ala-L-Asn-Ot-Bu

A white solid of Boc-L-Ala-L-Asn-Ot-Bu (345.4 mg) was obtained by the same method as in Example 1-4 except for L-Asn-Ot-Bu (manufactured by Watanabe Chemical Industries, Ltd., 188.2 mg, 1.0 mmol) in place of the Gly-Ot-Bu of Example 1-4 and addition of chloroform (0.5 mL). The yield was 96% and the diastereomeric ratio was >99:1.

Example 1-11: Production of Boc-L-Ala-L-His(Trt)-Ot-Bu

A white solid of Boc-L-Ala-L-His(Trt)-Ot-Bu (611.6 mg) was obtained by the same method as in Example 1-4 except for L-His(Trt)-Ot-Bu (manufactured by Watanabe Chemical Industries, Ltd., 453.6 mg, 1.0 mmol) in place of the Gly-Ot-Bu of Example 1-4. The yield was 98% and the diastereomeric ratio was >99:1.

Example 1-12: Production of Bz-L-Ala-L-Pro-Ot-Bu

A white solid of Bz-L-Ala-L-Pro-Ot-Bu (314.9 mg) was obtained by the same method as in Example 1-4 except for Bz-L-Ala-OH (manufactured by Watanabe Chemical Industries, Ltd., 386.4 mg, 2.0 mmol) in place of the Boc-L-Ala-OH of Example 1-4 and L-Pro-Ot-Bu (manufactured by Watanabe Chemical Industries, Ltd., 145.2 mg, 1.0 mmol) in place of the Gly-Ot-Bu of Example 1-4. The yield was 91% and the diastereomeric ratio was >99:1.

Example 1-13: Production of Boc-L-Asn(Trt)-L-Ala-Ot-Bu

Boc-L-Asn(Trt)-L-Ala-Ot-Bu (214.2 mg) was similarly obtained by the same method as in Example 1-1 except that Boc-L-Asn(Trt)-OH (manufactured by Watanabe Chemical Industries, Ltd., 949.2 mg, 2.0 mmol) was used in place of the Boc-L-Ala-OH of Example 1-1, the L-Ala-Ot-Bu-HCl (181.7 mg, 1.0 mmol) which was not neutralized was directly used in place of the L-Ala-Ot-Bu, DMSO (0.5 mL) was added, and the reaction temperature was changed to 40° C. The yield was 71% and the diastereomeric ratio was >99:1.

Example group 2: Production of an Amide Compound Via Amidation of a β-Homoamino Acid and an α-Amino Acid Example 2-1: Production of Boc-β-HoGly-L-Ile-Ot-Bu L-Ile-Ot-Bu-HCl (manufactured by Watanabe Chemical Industries, Ltd.) was neutralized with Amberlyst A21 free amine to obtain L-Ile-Ot-Bu.
Boc-β-HoGly-OH (manufactured by Watanabe Chemical Industries, Ltd., 182.9 mg, 1.0 mmol), L-Ile-Ot-Bu (manufactured by Watanabe Chemical Industries, Ltd., 93.6 mg, 0.5 mmol), 1-(trimethylsilyl)imidazole (154.3 mg, 1.1 mmol), and Ta(OMe)$_5$ (16.8 mg, 0.05 mmol) were put into a screw vial, which was covered with a screw cap and sealed under an argon atmosphere by the same procedures as in Example 1-1. The reaction was carried out in the same manner as in Example 1-1 except for stirring at a reaction temperature of 40° C. for 48 hours, whereby a white solid of Boc-β-HoGly-L-Ile-Ot-Bu (179.0 mg) was obtained. The yield was 99% and the diastereomeric ratio was >99:1.

Further, Boc-β-HoGly-L-Ile-Ot-Bu (178.9 mg) was similarly obtained via a reaction by the same method except that the L-Ile-Ot-Bu-HCl (111.9 mg, 0.5 mmol) was used directly without being neutralized in place of the L-Ile-Ot-Bu. The yield was >99% and the diastereomeric ratio was >99:1.

Example 2-2: Production of Bz-β-HoGly-L-Ile-Ot-Bu

A white solid of Bz-β-HoGly-L-Ile-Ot-Bu (175.5 mg) was obtained by the same method as in Example 2-1 except for Bz-β-HoGly-OH (manufactured by Tokyo Chemical Industry Co., Ltd., 193.2 mg, 1.0 mmol) in place of the Boc-β-HoGly-OH of Example 2-1. The yield was 97% and the diastereomeric ratio was >99:1.

Further, Bz-β-HoGly-L-Ile-Ot-Bu (175.5 mg) was similarly obtained via a reaction by the same method except that the L-Ile-Ot-Bu-HCl (111.9 mg, 0.5 mmol) of Example 2-1 was used directly without being neutralized in place of the L-Ile-Ot-Bu. The yield was 97% and the diastereomeric ratio was >99:1.

Example 2-3: Production of Boc-L-β-HoAla-L-Ala-Ot-Bu

A white solid of Boc-L-β-HoAla-L-Ala-Ot-Bu (160.1 mg) was obtained by the same method as in Example 2-1 except for Boc-L-β-HoAla-OH (manufactured by Combi-Blocks, Inc., 203.2 mg, 1.0 mmol) in place of the Boc-β-HoGly-OH of Example 2-1 and the L-Ala-Ot-Bu (72.6 mg, 0.5 mmol) of Example 1-1 in place of L-Ile-Ot-Bu. The yield was 97% and the diastereomeric ratio was >99:1.

Further, Boc-L-β-HoAla-L-Ala-Ot-Bu (160.0 mg) was similarly obtained via a reaction by the same method except that the L-Ala-Ot-Bu-HCl (90.8 mg, 0.5 mmol) of Example 1-1 was used directly without being neutralized in place of the L-Ala-Ot-Bu. The yield was 97% and the diastereomeric ratio was >99:1.

Example 2-4: Production of Boc-L-β-HoAla-L-Val-Ot-Bu

A white solid of Boc-L-β-HoAla-L-Val-Ot-Bu (174.7 mg) was obtained by the same method as in Example 2-1 except for Boc-L-β-HoAla-OH (manufactured by Combi-Blocks, Inc., 203.2 mg, 1.0 mmol) in place of the Boc-β-HoGly-OH of Example 2-1 and L-Val-Ot-Bu (manufactured by Combi-Blocks, Inc., 86.7 mg, 0.5 mmol) in place of L-Ile-Ot-Bu. The yield was 97% and the diastereomeric ratio was >99:1.

Further, Boc-L-β-HoAla-L-Val-Ot-Bu (174.8 mg) was similarly obtained via a reaction by the same method except that L-Val-Ot-Bu-HCl (manufactured by Watanabe Chemical Industries, Ltd., 104.9 mg, 0.5 mmol) was used directly without being neutralized in place of the L-Val-Ot-Bu. The yield was 97% and the diastereomeric ratio was >99:1.

Example 2-5: Production of Boc-L-β-HoPhe-L-Ser(t-Bu)-Ot-Bu

A white solid of Boc-L-β-HoPhe-L-Ser(t-Bu)-Ot-Bu (238.1 mg) was obtained by the same method as in Example 2-1 except that Boc-L-β-HoPhe-OH (manufactured by Watanabe Chemical Industries, Ltd., 279.3 mg, 1.0 mmol) was used in place of the Boc-β-HoGly-OH of Example 2-1, L-Ser(t-Bu)-Ot-Bu (manufactured by Watanabe Chemical Industries, Ltd., 108.7 mg, 0.5 mmol) was used in place of L-Ile-Ot-Bu, and the reaction temperature was changed to 50° C. The yield was 99% or more and the diastereomeric ratio was >99:1.

Further, a reaction was carried out by a similar method using L-Ser(t-Bu)-Ot-Bu-HCl (manufactured by Watanabe Chemical Industries, Ltd., 126.9 mg, 0.5 mmol) directly without being neutralized in place of the L-Ser(t-Bu)-Ot-Bu, whereby Boc-L-β-HoPhe-L-Ser(t-Bu)-Ot-Bu (239.0 mg) was similarly obtained. The yield was >99% and the diastereomeric ratio was >99:1.

Example 2-6: Production of Boc-L-β-HoPhg-L-Lys(Boc)-Ot-Bu

L-Lys(Boc)-Ot-Bu-HCl (manufactured by Watanabe Chemical Industries, Ltd.) was neutralized with Amberlyst A21 free amine to obtain L-Lys(Boc)-Ot-Bu.
A white solid of Boc-L-β-HoPhg-L-Lys(Boc)-Ot-Bu (266.5 mg) was obtained by the same method as in Example 2-1 except that Boc-L-β-HoPhg-OH (manufactured by Watanabe Chemical Industries, Ltd., 265.3 mg, 1.0 mmol) was used in place of the Boc-β-HoGly-OH of Example 2-1, the L-Lys(Boc)-Ot-Bu (151.1 mg, 0.5 mmol) was used in place of L-Ile-Ot-Bu, and the reaction temperature was changed to 50° C. The yield was 97% or more and the diastereomeric ratio was >99:1.

Further, a reaction was carried out by a similar method using the L-Lys(Boc)-Ot-Bu-HCl (manufactured by Watanabe Chemical Industries, Ltd., 169.4 mg, 0.5 mmol) directly without being neutralized in place of the L-Lys (Boc)-Ot-Bu, whereby Boc-L-β-HoPhg-L-Lys(Boc)-Ot-Bu (265.2 mg) was similarly obtained. The yield was 96% and the diastereomeric ratio was >99:1.

Example 2-7: Production of
Boc-L-β-HoMet-L-Leu-Ot-Bu

L-Leu-Ot-Bu-HCl (manufactured by Watanabe Chemical Industries, Ltd.) was neutralized with Amberlyst A21 free amine to obtain L-Leu-Ot-Bu.

A white solid of Boc-L-β-HoMet-L-Leu-Ot-Bu (203.3 mg) was obtained by the same method as in Example 2-1 except for using Boc-L-β-HoMet-OH (manufactured by Combi-Blocks, Inc., 263.4 mg, 1.0 mmol) in place of the Boc-β-HoGly-OH of Example 2-1 and the L-Leu-Ot-Bu (93.6 mg, 0.5 mmol) in place of L-Ile-Ot-Bu. The yield was 94% and the diastereomeric ratio was >99:1.

Further, a reaction was carried out by a similar method using the L-Leu-Ot-Bu-HCl (manufactured by Watanabe Chemical Industries, Ltd., 111.9 mg, 0.5 mmol) directly without being neutralized in place of the L-Leu-Ot-Bu, whereby Boc-L-β-HoMet-L-Leu-Ot-Bu (210.8 mg) was similarly obtained. The yield was 97% and the diastereomeric ratio was >99:1.

Example Group 3: Production of an Amide Compound Via Amidation of Three α-Amino Acids Example 3-1: Production of
Boc-L-Ala-L-Ala-L-Ala-Ot-Bu L-Ala-OMe-HCl (manufactured by Watanabe Chemical Industries, Ltd.) was neutralized with Amberlyst A21 free amine to obtain L-Ala-OMe.

In a glove box under an argon atmosphere, Boc-L-Ala-OH (manufactured by Watanabe Chemical Industries, Ltd., 94.6 mg, 0.50 mmol), the L-Ala-OMe (26.8 mg, 0.25 mmol), 1-(trimethylsilyl)imidazole (70.1 mg, 0.50 mmol), and Ta(OMe)$_5$ (8.40 mg, 0.025 mmol) together with a stirrer were put into a dried 5-mL screw vial, which was covered with a screw cap and sealed under the argon atmosphere. This screw vial was removed from the glove box and placed in an oil bath. After stirring at a reaction temperature of 60° C. for 24 hours, the screw vial was removed and allowed to cool to ambient temperature. The reaction product obtained in the screw vial was diluted with chloroform (20 mL), transferred with distilled water (20 mL) into a separating funnel, and extracted twice using chloroform (20 mL). The extract was dried using anhydrous magnesium sulfate and subsequently filtered to collect a filtrate. The filtrate was transferred to a 5-mL screw vial and the solvent was removed from the filtrate by distillation using a rotary evaporator to obtain Boc-L-Ala-L-Ala-OMe.

Next, in a glove box under an argon atmosphere, L-Ala-Ot-Bu (72.5 mg, 0.50 mmol) obtained by the method described in Example 1-1, 2,2':6',2":6",2'''-quaterpyridine (synthesized in accordance with the method described in Wachter et al., Chem. Commun. 2016, 52[66]: 10121-10124, 7.8 mg, 0.025 mmol), and Ta(OMe)$_5$ (8.40 mg, 0.025 mmol) were put into a container of the obtained Boc-L-Ala-L-Ala-OMe, which was covered with a screw cap and sealed under the argon atmosphere. This screw vial was removed from the glove box and placed in an oil bath. After stirring at a reaction temperature of 70° C. for 48 hours, the screw vial was removed and allowed to cool to ambient temperature. The reaction product obtained in the screw vial was diluted with chloroform (13 mL) and purified by flash silica gel column chromatography (ethyl acetate/n-hexane). Thereafter, the solvent was removed by distillation using an evaporator, whereby a white solid of Boc-L-Ala-L-Ala-L-Ala-Ot-Bu (80.4 mg) was obtained. The yield was 83% and the diastereomer ratio was >99:1.

Example 3-2: Production of
Boc-L-Leu-L-Ala-L-Ala-Ot-Bu

A white solid of Boc-L-Leu-L-Ala-L-Ala-Ot-Bu (97.5 mg) was obtained by the same procedures as in Example 3-1 except for Boc-Leu-OH (manufactured by Watanabe Chemical Industries, Ltd., 115.5 mg, 0.5 mmol) in place of the Boc-L-Ala-OH of Example 3-1. The yield was 91% and the diastereomeric ratio was >99:1.

Example 3-3: Production of
Boc-L-Phe-L-Ala-L-Ala-Ot-Bu

A white solid of Boc-L-Phe-L-Ala-L-Ala-Ot-Bu (96.1 mg) was obtained by the same procedures as in Example 3-1 except for Boc-Phe-OH (manufactured by Watanabe Chemical Industries, Ltd., 140.1 mg, 0.5 mmol) in place of the Boc-L-Ala-OH of Example 3-1. The yield was 83% and the diastereomeric ratio was >99:1.

Example 3-4: Production of
Cbz-Gly-L-Ala-L-Ala-Ot-Bu

A white solid of Cbz-Gly-L-Ala-L-Ala-Ot-Bu (92.6 mg) was obtained by the same procedures as in Example 3-1 except for Cbz-Gly-OH (manufactured by Watanabe Chemical Industries, Ltd., 104.5 mg, 0.5 mmol) in place of the Boc-L-Ala-OH of Example 3-1. The yield was 91% and the diastereomeric ratio was >99:1.

Example 3-5: Production of
Boc-L-Ala-L-Leu-Gly-Ot-Bu

L-Leu-OMe-HCl (manufactured by Watanabe Chemical Industries, Ltd.) and Gly-Ot-Bu-HCl (manufactured by Watanabe Chemical Industries, Ltd.) were neutralized with Amberlyst A21 free amine to obtain L-Leu-OMe and Gly-Ot-Bu, respectively.

Boc-L-Ala-L-Leu-OMe was synthesized by the same method as in Example 3-1 except for the L-Leu-OMe (36.3 mg, 0.25 mmol) in place of the L-Ala-OMe of Example 3-1, and subsequently, a white solid of Boc-L-Ala-L-Leu-Gly-Ot-Bu (91.3 mg) was obtained by the same procedures as in Example 3-1 except for the Gly-Ot-Bu (65.5 mg, 0.50 mmol) in place of L-Ala-Ot-Bu. The yield was 88% and the diastereomeric ratio was >99:1.

Example 3-6: Production of
Boc-L-Ala-L-Met-L-Ala-Ot-Bu

L-Met-OMe-HCl (manufactured by Watanabe Chemical Industries, Ltd.) was neutralized with Amberlyst A21 free amine to obtain L-Met-OMe.

A white solid of Boc-L-Ala-L-Met-Ala-Ot-Bu (101.0 mg) was obtained by the same method as in Example 3-1 except for the L-Met-OMe (40.8 mg, 0.25 mmol) in place of the L-Ala-OMe of Example 3-1. The yield was 91% and the diastereomeric ratio was >99:1.

Example 3-7: Production of Boc-L-Ala-L-Ala-L-Val-Ot-Bu

L-Val-Ot-Bu-HCl (manufactured by Watanabe Chemical Industries, Ltd.) was neutralized with Amberlyst A21 free amine to obtain L-Val-Ot-Bu.

A white solid of Boc-L-Ala-L-Ala-L-Val-Ot-Bu (84.1 mg) was obtained by the same procedures as in Example 3-1 except for the L-Val-Ot-Bu (manufactured by Watanabe Chemical Industries, Ltd., 130.1 mg, 0.75 mmol) in place of the L-Ala-Ot-Bu of Example 3-1. The yield was 81% and the diastereomeric ratio was >99:1.

Example 3-8: Production of Boc-L-Ala-L-Ala-L-Met-Ot-Bu

L-Met-Ot-Bu-HCl (manufactured by Watanabe Chemical Industries, Ltd.) was neutralized with Amberlyst A21 free amine to obtain L-Met-Ot-Bu.

A white solid of Boc-L-Ala-L-Ala-L-Met-Ot-Bu (106.1 mg) was obtained by the same procedures as in Example 3-1 except for the L-Leu-Ot-Bu (manufactured by Watanabe Chemical Industries, Ltd., 103.1 mg, 0.50 mmol) in place of the L-Ala-Ot-Bu of Example 3-1. The yield was 95% and the diastereomeric ratio was >99:1.

Example 3-9: Production of Boc-Gly-Gly-Gly-L-Ala-L-Ala-Ot-Bu

In a glove box under an argon atmosphere, Boc-Gly-Gly-Gly-OH (manufactured by Watanabe Chemical Industries, Ltd., 144.6 mg, 0.50 mmol), Ala-L-Ala-Ot-Bu (54.1 mg, 0.25 mmol), 1-(trimethylsilyl)imidazole (77.1 mg, 0.55 mmol), Ti(Oi-Pr)$_4$ (manufactured by Sigma-Aldrich Co., 3.6 mg, 0.0125 mmol), and CHCl$_3$ (0.25 mL) together with a stirrer were put into a dried 5-mL screw vial, which was covered with a screw cap and sealed under the argon atmosphere. This screw vial was removed from the glove box and placed in an oil bath. After stirring at a reaction temperature of 50° C. for 72 hours, the screw vial was removed and allowed to cool to ambient temperature.

The reaction product obtained in the screw vial was diluted with chloroform (15 mL) and purified by flash silica gel column chromatography (methanol/chloroform). Thereafter, the solvent was removed by distillation using an evaporator, whereby Boc-Gly-Gly-Gly-L-Ala-L-Ala-Ot-Bu (121.4 mg) was obtained. The yield was 99% and the diastereomer ratio was >99:1.

Reference Example Group: Examination of Reaction Mechanism

Reference Example 1

A reaction was carried out for 24 hours in the same method described in the first half of Example 2-4 except that L-Val-Ot-Bu and Ta(OMe)$_5$ were not used, in other words, only Boc-L-β-HoAla-OH (203.2 mg, 1.0 mmol) and 1-(trimethylsilyl)imidazole (154.3 mg, 1.1 mmol) were used. A part of the obtained reaction mixture was dissolved in deuterochloroform. $^1$H-NMR measurement and 29Si-NMR measurement were carried out.

In the $^1$H-NMR measurement and 29Si-NMR measurement, the measuring device is JEOL 400SS (manufactured by JEOL Ltd.) and the measurement solvent was CDCl$_3$. $^1$H-NMR were measured at 400 MHz and 29Si-NMR were measured at 80 MHz. Chemical shifts are given in ppm. The solvent resonance was used as the internal standard (1H-NMR: chloroform, 7.26 ppm as the internal standard and 29Si-NMR: tetramethylsilane, 0 ppm as the internal standard).

Figure 1B:
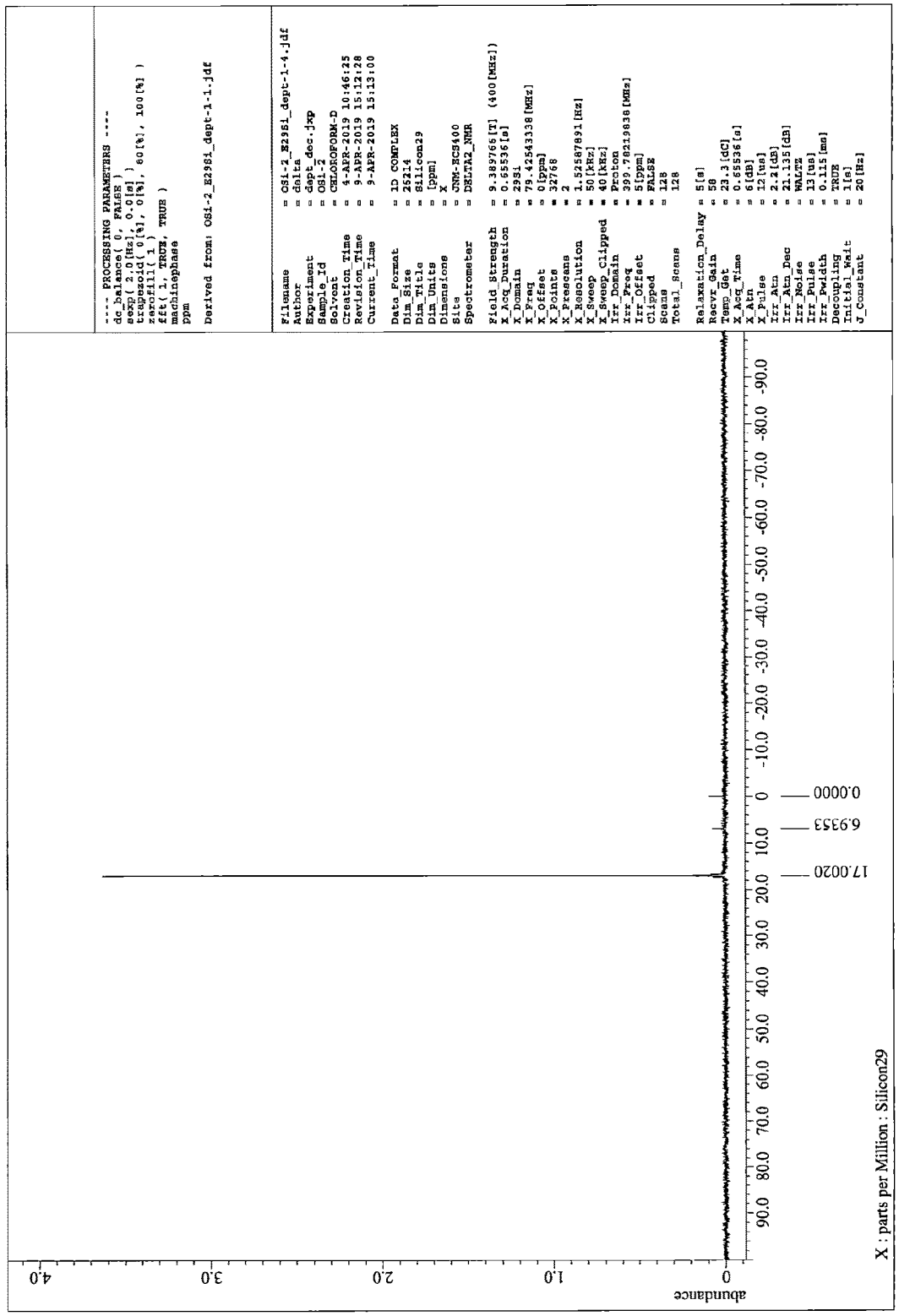
FIG. 1B depicts a $^{29}$Si-NMR spectrum obtained in Reference Example 1.

FIG. 1A and FIG. 1B depict a $^1$H-NMR spectrum and a $^{29}$Si-NMR spectrum, respectively. These results confirmed that Boc-L-β-HoAla-OTMS was formed. $^1$H-NMR (400 MHz, CDCl$_3$) δ 5.20-4.95 (m, 1H, NH), 4.10-3.90 (m, 1H, BocNHCH(CH$_3$)CH$_2$), 2.48 (dd, J=15.6, 5.5 Hz, 1H, Boc-NHCH(CH$_3$)CH$_2$), 2.41 (dd, J=15.6, 6.4 Hz, 1H, BocNHCH(CH$_3$)CH$_2$), 1.39 (s, 9H, (CH$_3$)$_3$COCONHCH(CH$_3$)CH$_2$), 1.16 (d, J=6.9 Hz, 3H, BocNHCH(CH$_3$)CH$_2$), 0.24 (s, 9H, CO$_2$Si(CH$_3$)$_3$). $^{29}$Si-NMR (80 MHz, CDCl$_3$) δ 17.00.

Reference Example 2

A reaction was carried out for 48 hours in the same method described in the first half of Example 2-4 except that Ta(OMe)$_5$ was not used, in other words, only Boc-L-β-HoAla-OH (203.2 mg, 1.0 mmol), 1-(trimethylsilyl)imidazole (154.3 mg, 1.1 mmol), and L-Val-Ot-Bu (86.7 mg, 0.50 mmol) were used. A part of the obtained reaction mixture was dissolved in deuterochloroform. $^1$H-NMR measurement and 29Si-NMR measurement were carried out.

Figure 2A:
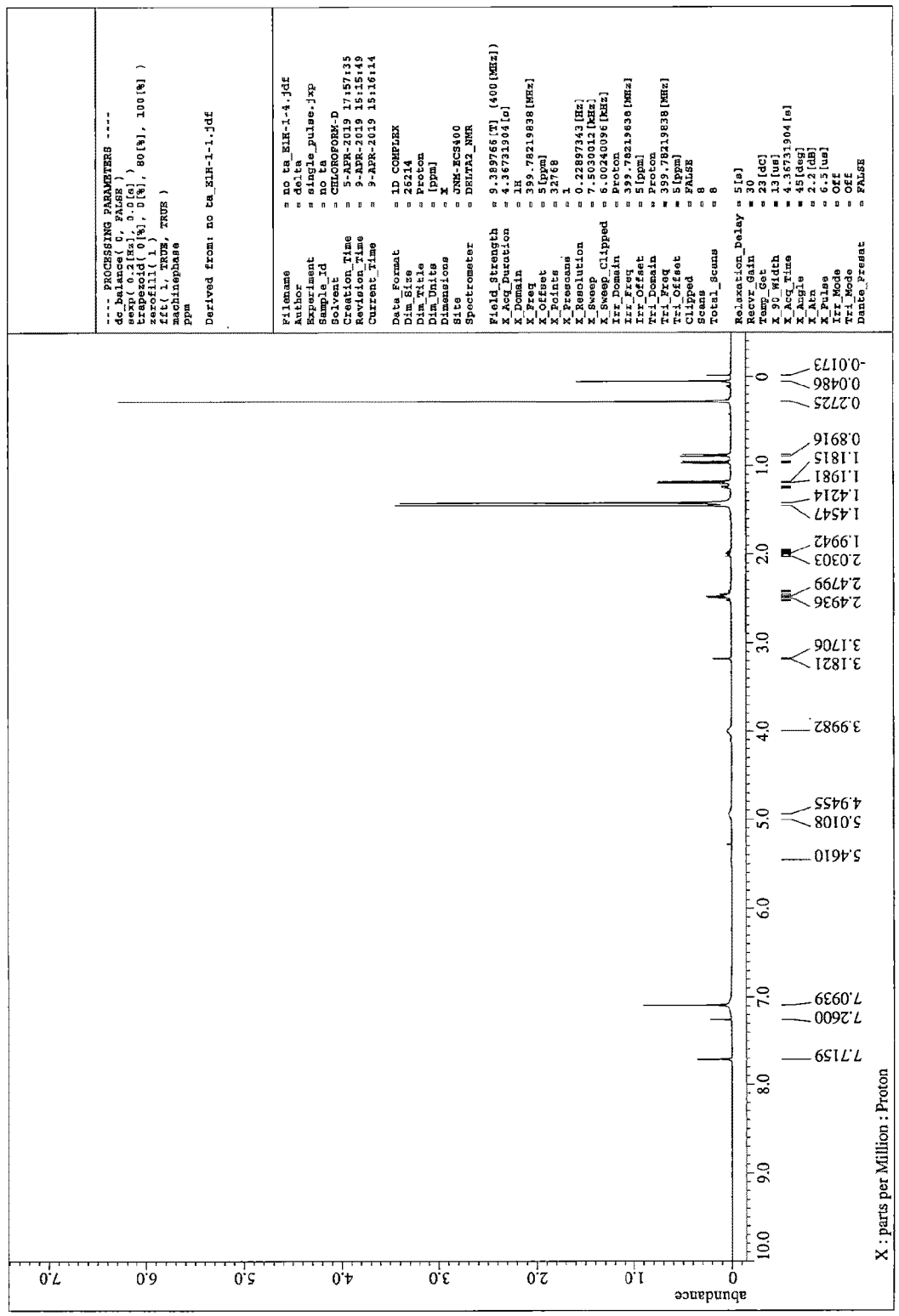
FIG. 2A depicts a $^1$H-NMR spectrum obtained in Reference Example 2.
Figure 2B:
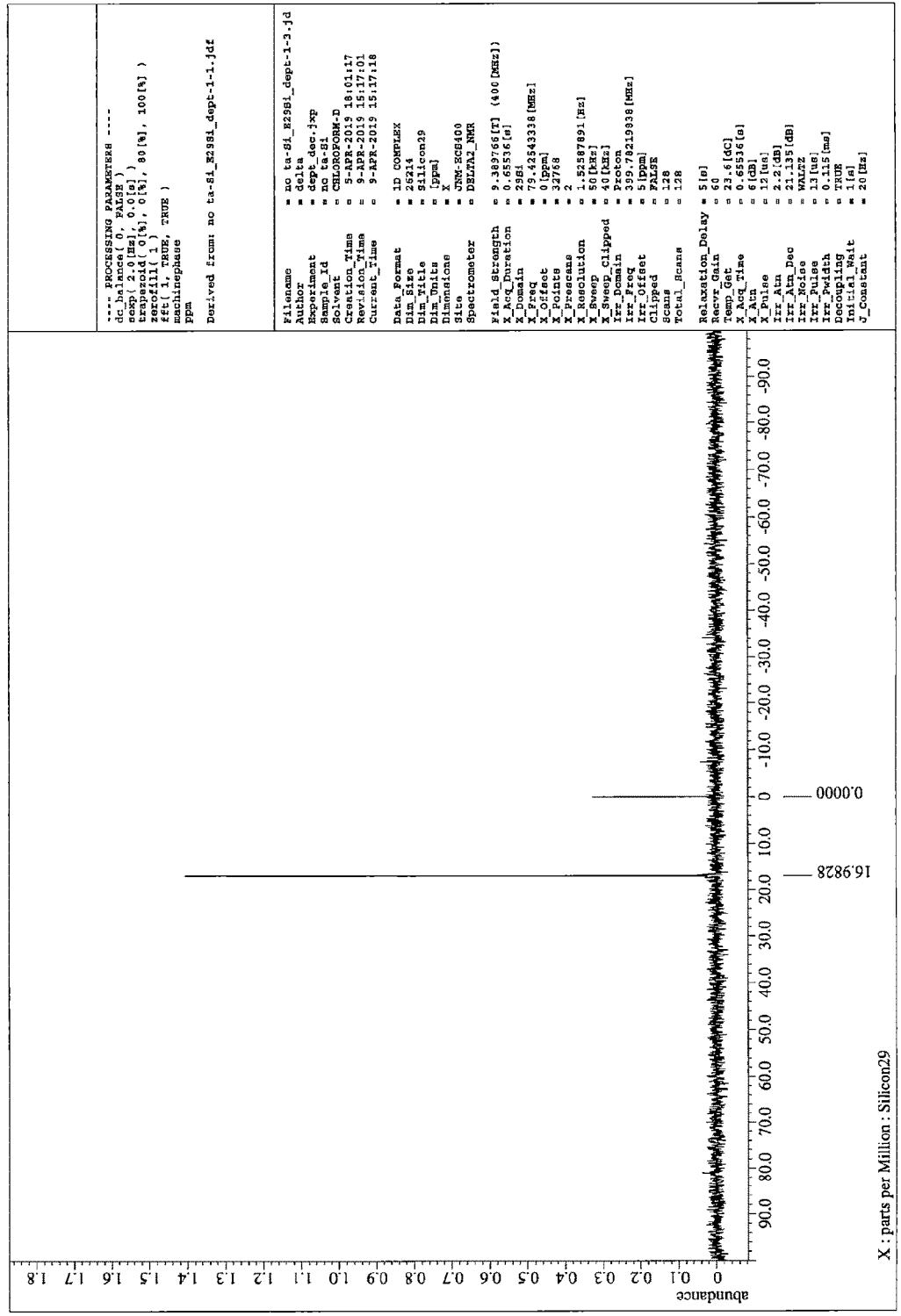
FIG. 2B depicts a $^{29}$Si-NMR spectrum obtained in Reference Example 2.

FIG. 2A and FIG. 2B depict a H-NMR spectrum and a $^{29}$Si-NMR spectrum, respectively. These results confirmed the presence of Boc-L-β-HoAla-OTMS and unreacted L-Val-Ot-Bu. Boc-L-β-HoAla-L-Val-Ot-Bu, which is the final product of the method described in the first half of Example 2-4, was not confirmed.

Discussion

Reference Example 1 reveals that in the method of the invention of the present application, the action of a silylating agent on a compound of general formula (1) results in silylesterification of the carboxyl group of the compound of general formula (1). Further, Reference Example 2 reveals that only the action of a silylating agent on a compound of general formula (1) and a compound of general formula (2) results in silylesterification of the carboxyl group of the compound of general formula (1) but does not promote a reaction with the amino group of the compound of general formula (2). In other words, it is revealed that the coexistence of a silylating agent and a Lewis acid catalyst is required for silylesterification of the carboxyl group of a compound of general formula (1) followed by formation of an amide bond to the amino group of a compound of general formula (2).

The invention claimed is:

1. A method for producing an amide compound, comprising a step of forming an amide bond between a carboxyl group on the right side of general formula (1) of a compound represented by general formula (1) and an amino group on the left side of general formula (2) of a compound represented by general formula (2) in the presence of a Lewis acid catalyst and a silylating agent to synthesize a compound represented by general formula (3),

[Chem. 1]

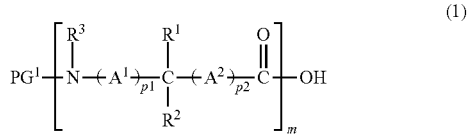

-continued

[Chem. 2]

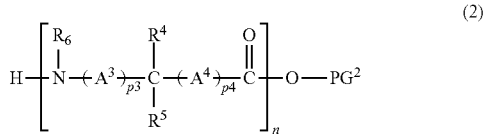

(2)

[Chem. 3]

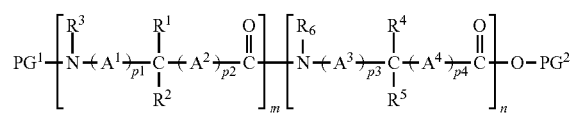

(3)

wherein, in general formulas (1), (2), and (3), $R^1$, $R^2$, $R^4$, and $R^5$ each independently represent a hydrogen atom, halogen atom, hydroxy group, carboxyl group, nitro group, cyano group, or thiol group, or a monovalent hydrocarbon group or heterocyclic group, which may have one, two, or more substituents, where the monovalent hydrocarbon group or heterocyclic group may be bonded to a nitrogen atom via a linker group;

$R^3$ and $R^6$ each independently represent a hydrogen atom, carboxyl group, or hydroxy group, or a monovalent hydrocarbon group or heterocyclic group, which may have one, two, or more substituents, where the monovalent hydrocarbon group or heterocyclic group may be bonded to a carbon atom via a linker group;

$R^1$ and $R^3$ may be bonded together to form, together with a carbon atom to which $R^1$ bonds and a nitrogen atom to which $R^3$ bonds, a heterocycle which may have one, two, or more substituents, or $R^4$ and $R^6$ may be bonded together to form, together with a carbon atom to which $R^4$ bonds and a nitrogen atom to which $R^6$ bonds, a heterocycle which may have one, two, or more substituents;

$A^1$ to $A^4$ each independently represent a divalent aliphatic hydrocarbon group having 1 to 3 carbon atoms, which may have one, two, or more substituents;

p1 to p4 each independently represent 0 or 1;

m and n are each independently an integer of 1 or higher and represent the number of constitutional units represented by a structure in [ ];

$PG^1$ represents a protecting group of an amino group;

$PG^2$ represents a protecting group of a carboxyl group; and an amino group on the left side of general formula (2) may form a salt with an acid, wherein the Lewis acid catalyst is a metal catalyst, the metal catalyst is a compound containing one or more metals selected from the group consisting of titanium, zirconium, hafnium, tantalum, and niobium, and the silylating agent is one or more compounds selected from the group consisting of silylimidazole compounds, silyltriazole compounds, silylhalide compounds, silylamide compounds, and silylamine compounds.

2. The method according to claim 1, wherein the $PG^1$ represents a monovalent hydrocarbon group or heterocyclic group, which may have one, two, or more substituents, provided that a linker group may be present between the hydrocarbon group or heterocyclic group and the nitrogen atom of an amino group to which the $PG^1$ bonds.

3. The method according to claim 1, wherein the step is carried out at a temperature of 60° C. or lower.

4. The method according to claim 1, further comprising deprotecting the amino group protected by the $PG^1$ and the carboxyl group protected by $PG^2$ after formation of the amide bond.

5. The method according to claim 1, wherein the silylating agent comprises a silylimidazole compound.

6. The method according to claim 5, wherein the silylimidazole compound is a compound represented by the following general formula (4-1):

[Chem. 4-1]

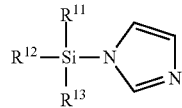

(4-1)

wherein, in general formula (4-1), $R^{11}$ to $R^{13}$ each independently represent a linear or branched-chain alkyl group or alkoxy group with 1 to 10 carbons, which may have one, two, or more substituents.

* * * * *